(12) United States Patent
Agou et al.

(10) Patent No.: US 11,884,708 B2
(45) Date of Patent: Jan. 30, 2024

(54) STAPLED PEPTIDE INHIBITORS OF NEMO AS POTENTIAL ANTI-INFLAMMATORY AND ANTI-CANCER DRUGS

(71) Applicant: INSTITUT PASTEUR, Paris (FR)

(72) Inventors: Fabrice Agou, Paris (FR); Alix Boucharlat, Paris (FR); Yves-Marie Coic, Meudon (FR); Françoise Baleux, Paris (FR)

(73) Assignee: INSTITUT PASTEUR, Paris (FR)

( * ) Notice: Subject to any disclaimer, the term of this patent is extended or adjusted under 35 U.S.C. 154(b) by 0 days.

(21) Appl. No.: 17/487,904

(22) Filed: Sep. 28, 2021

(65) Prior Publication Data

US 2022/0025002 A1    Jan. 27, 2022

Related U.S. Application Data

(63) Continuation of application No. 15/776,481, filed as application No. PCT/EP2016/082390 on Dec. 22, 2016, now Pat. No. 11,149,070.

(30) Foreign Application Priority Data

Dec. 23, 2015    (EP) .................................... 15307137

(51) Int. Cl.
*C07K 14/47* (2006.01)
*A61K 38/00* (2006.01)

(52) U.S. Cl.
CPC .......... *C07K 14/4702* (2013.01); *A61K 38/00* (2013.01); *C07K 2319/03* (2013.01)

(58) Field of Classification Search
None
See application file for complete search history.

(56) References Cited

U.S. PATENT DOCUMENTS 11,149,070 B2 * 10/2021 Agou ................. C07K 14/4702

FOREIGN PATENT DOCUMENTS

| WO | WO 2005/027959 A1 | 3/2005 |
| WO | WO 2010/034026 A1 | 3/2010 |
| WO | WO 2014/150350 A1 | 9/2014 |

OTHER PUBLICATIONS

Verdine et al., Stapled Peptides for Intracellular Drug Targets, Mthods in Enzymology 503, 3-33.
Yoshikawa et al., Crystal structure ofthe NEMO ubiquitin-biinding domain in complex with Lys 63-linked di-ubiquitin, FEBS Letters 583 (2009) 3317-3322.
Rahighi et al., Specific Recogntion of Linear Ubiquitin Chains by NEMO Is Important for NF-kB Activation, Cell 136, 1098-1109, Mar. 20, 2009.

* cited by examiner

*Primary Examiner* — Christina Bradley
(74) *Attorney, Agent, or Firm* — Arrigo, Lee, Guttman & Mouta-Bellum LLP

(57) ABSTRACT

The invention concerns stapled peptide inhibitors of NEMO which inhibit the Nuclear Factor κB (NF-κB) signaling pathway and are useful as medicine candidates, in particular as anti-inflammatory or anticancer drugs.

Figure 1A:
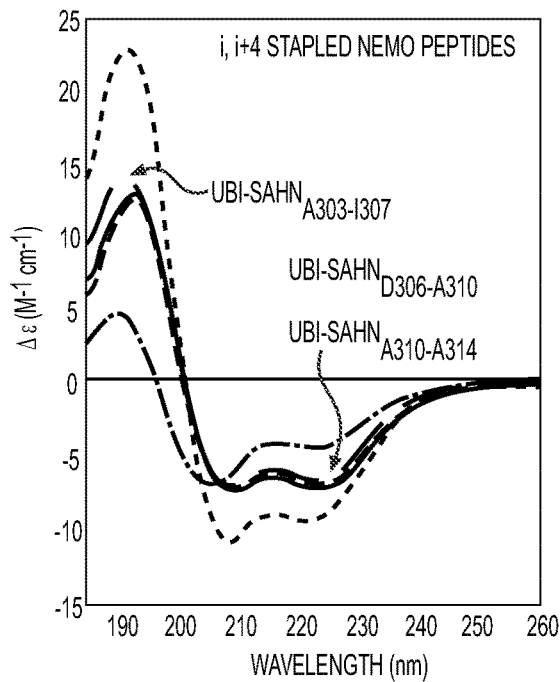

15 Claims, 13 Drawing Sheets
Specification includes a Sequence Listing.

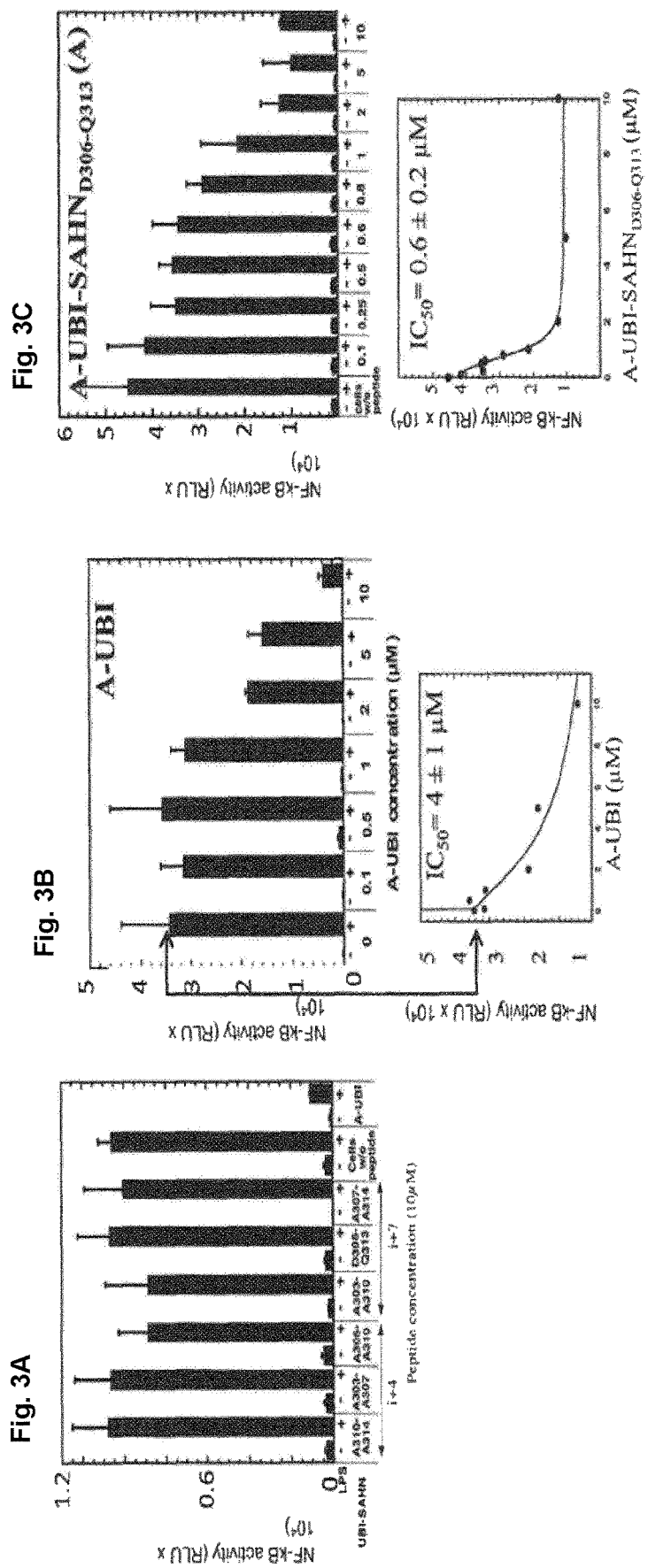

STAPLED PEPTIDE INHIBITORS OF NEMO AS POTENTIAL ANTI-INFLAMMATORY AND ANTI-CANCER DRUGS

SEQUENCE LISTING

The instant application contains a Sequence Listing which has been submitted electronically in ASCII format and is hereby incorporated by reference in its entirety. Said ASCII copy, created on Oct. 1, 2018, is named F226EP212_ST25_1.txt and is 11,322 bytes in size.

BACKGROUND OF THE INVENTION

The invention concerns stapled peptide inhibitors of NEMO which inhibit the Nuclear Factor κB (NF-κB) signaling pathway and are useful as medicine candidates, in particular as anti-inflammatory or anticancer drugs.

Prolonged activation and aberrant regulation of the NF-κB signaling pathway are associated with many cancers as well as severe autoimmune and chronic inflammatory diseases making its inhibition an attractive target for anti-inflammatory and anti-cancer therapies.

In this regard, NF-κB essential modulator (NEMO) is a promising therapeutic target for inhibitors because this protein is a central and non-redundant component of the IκB kinase (IKK) complex. Furthermore, NEMO but not its kinase partners IKKα and β, negatively regulates TNF-mediated apoptosis and -regulated necrosis independently of NF-κB, making NEMO a more attractive target than kinase components of IKK complex to promote tumor death in cancer therapy. In addition, targeting NEMO may have less toxicity side effects in animal models compared with kinase inhibitors of IKK.

The NEMO protein (419 amino acids in human; UniProt Q9Y6K9) is composed of several overlapping functional domains: the N-terminal IKK-binding domain, the minimal coiled-coil motif 2 and leucine zipper (CC2-LZ) oligomerization domain that is required for binding to K63-linked and linear ubiquitin chains (also called M1-linked chains), and the C-terminal zinc finger (ZF) motif, which represents a second ubiquitin binding domain (UBD). The LZ domain of NEMO contains a region of high homology which has been identified in four other proteins: Optineurin and ABIN 1, 2, and 3. This region is named NOA (Nemo Optineurin Abin), but is also referred to as NUB/UBAN. The NOA region binds to K63-linked and linear ubiquitin chains. The NOA ubiquitin binding site itself can only interact weakly with K63-linked or linear ubiquitin chains and exhibits more efficient binding in the context of the full CC2-LZ domain.

NEMO triggers NF-κB/IKK activation through its specific interaction with linear and K63-linked polyubiquitin chains. Thus, the identification of NEMO inhibitors by targeting the NEMO-ubiquitin interface provides a strategy for the design of new anti-inflammatory and anti-cancer therapies.

The inventors have previously described a peptide inhibitor of NEMO derived from the NOA ubiquitin site, named UBI for ubiquitin binding inhibitor ([1] and WO 2005/02795). UBI (SEQ ID NO: 1) corresponds to residues 301 to 321 of the human sequence and contains an Asp to Arg residue substitution at position 311. UBI inhibits NF-κB signaling pathway by preferentially blocking interaction between K63-tetraubiquitin chains and the NOA UBD of the CC2-LZ domain of NEMO.

Now the inventors have designed and synthesized UBI-derived stapled peptides with improved properties compared to UBI.

Therefore, the invention relates to a peptide, comprising at least an amino sequence (I) which is at least 60%, preferably at least 65%, 70%, 75%, 80%, 85%, 90% or 95% identical to the amino acid sequence SEQ ID NO: 1, and further comprising at least one macrocycle-forming linker connecting a first amino acid to a second amino acid of said sequence (I).

The peptide of the invention is a cross-linked or stapled peptide. The first and the second amino acids are cross-linked amino acids.

The stapled peptide of the invention is a peptide inhibitor of NEMO which inhibits the NF-κB signaling pathway or a precursor of said peptide inhibitor which becomes an active peptide inhibitor when linked to a Cell-penetrating peptide (CPP).

The stapled peptide of the invention has an increased thermal stability, α-helicity, binding affinity for the CC2-LZ domain of NEMO and NF-κB inhibitory activity compared to UBI. In addition, as opposed to UBI which requires a cell-penetration-peptide for binding to the CC2-LZ domain of NEMO and NF-κB inhibition activity, some peptides of the invention are capable of penetrating into cells and inhibiting efficiently the NF-κB signaling pathway; such peptides could overcome the cell-toxicity and poor serum stability observed with some Cell Penetrating Peptide sequences. Furthermore, the peptide of the invention is also very potent at inducing cell death of human cancer cells characterized by NF-κB hyperactivation, compared to IKKβ inhibitors which are much less potent. Cell-death induced by the peptide of the invention is not only very efficient but also very rapid and specific. Furthermore, the induction of cell-death by necrosis rather than apoptosis should increase the anti-inflammatory effect of the peptide of the invention.

In view of its improved properties, the peptide of the invention represents a promising drug candidate for the treatment of diseases characterized by a prolonged activation and/or aberrant regulation of the NF-κB signaling pathway such as many cancers as well as severe autoimmune and chronic inflammatory diseases.

The various properties and activities of the peptide of the invention can be verified by standard assays which are well-known in the art such as those described in the examples of the present application.

Definitions

In the following description:
- "a", "an", and "the" include plural referents, unless the context clearly indicates otherwise. As such, the term "a" (or "an"), "one or more" or "at least one" can be used interchangeably herein.
- The standard one letter amino acid code is used.
- The first amino acid is situated at a position which is closer to the N-terminus of the peptide compared to the position of the second peptide, which means that the position number of the first peptide in the peptide sequence is inferior or lower to that of the second peptide which is higher or superior, using the conventional numbering of amino acid positions in peptide sequence (e.g., from the N-terminus to the C-terminus of the peptide sequence).
- The percent amino acid sequence identity is defined as the percent of amino acid residues in a Compared Sequence that are identical to the Reference Sequence (SEQ ID NO: 1) after aligning the sequences and introducing gaps if necessary, to achieve the maximum sequence identity. The Percent identity is then determined according to the following formula: Percent identity=100×[1−(C/R)], wherein C is the number of differences between the Reference Sequence and the Compared sequence over the entire length of the Reference sequence, wherein (i) each amino acid in the Reference Sequence that does not have a corresponding aligned amino acid in the Compared Sequence, (ii) each gap in the Reference Sequence, and (iii) each aligned amino acid in the Reference Sequence that is different from an amino acid in the Compared Sequence constitutes a difference; and R is the number amino acids in the Reference Sequence over the length of the alignment with the Compared Sequence with any gap created in the Reference Sequence also being counted as an amino acid. Alignment for purposes of determining percent amino acid sequence identity can be achieved in various ways known to a person of skill in the art, for instance using publicly available computer software such as BLAST[2]. When using such software, the default parameters, e.g., for gap penalty and extension penalty, are preferably used. For amino acid sequences, the BLASTP program uses as default a word length (W) of 3 and an expectation (E) of 10.

"macrocycle" refers to a molecule having a chemical structure including a ring or cycle formed by at least 9 covalently bonded atoms.

"Amino acid" refers to a molecule containing both an amino group and a carboxyl group. The term amino acid includes α-amino acids, natural amino acids (D- and -L isomers), non-naturally amino acids and amino acid analogs.

The sequence (I) corresponds to the sequence which binds to the NOA region within the CC2-LZ domain of NEMO.

In some embodiments, the sequence (I) is selected from the group consisting of SEQ ID NO: 1 and a sequence which differs from SEQ ID NO: 1 by deletion(s), insertion(s), and/or of substitution(s) of up to eight amino acids in total, preferably up to five amino acids. Therefore, the sequence (I) consists of 12 to 28 amino acids, usually 15 to 25 amino acids.

In some embodiments, the amino acid substitution(s) in SEQ ID NO:1 is (are) advantageously chosen from conservative substitutions, i.e., substitutions of one amino acid with another having similar chemical or physical properties (size, charge or polarity), which substitution generally does not adversely affect the biochemical, biophysical and/or biological properties of the peptide. In particular, the substitution does not disrupt the interaction of the peptide with the CC2-LZ domain of NEMO. More preferably, said conservative substitution(s) are chosen within one of the following five groups: Group 1-small aliphatic, non-polar or slightly polar residues (A, S, T, P, G); Group 2-polar, negatively charged residues and their amides (D, N, E, Q); Group 3-polar, positively charged residues (H, R, K); Group 4-large aliphatic, nonpolar residues (M, L, I, V, C); and Group 5-large, aromatic residues (F, Y, W).

In other embodiments, the amino acid substitution(s) in SEQ ID NO: 1 are advantageously chosen from non-conservative substitutions, i.e., substitutions of one amino acid with another which has different chemical or physical properties (size, charge or polarity), wherein the substitution improves the biochemical, biophysical and/or biological properties of the peptide.

In some preferred embodiments, the peptide comprises the substitution of one to three negatively charged amino acids of SEQ ID NO: 1, chosen from D6, E15 and E20 with a neutral amino acid or basic amino acid; the positions are indicated by reference to the amino acid numbering in SEQ ID NO: 1 and correspond to D306, E315 and E320 in human NEMO amino acid sequence. These substitutions provide some cell penetration capability to the peptide compared to UBI which is unable to penetrate into cells in the absence of a cell-penetration-peptide. The acidic residues are advantageously replaced with an amino acid chosen from Glutamine (Q), Glutamic acid methyl ester or (GluOMe), Alanine, Lysine, and Arginine. Preferably, the peptide comprises the substitution of the three residues D6, E15 and E20.

In some preferred embodiments, the sequence (I) differs from SEQ ID NO: 1 by up to eight amino acid substitutions, preferably by one to five amino acid substitutions; more preferably the sequence (I) includes the substitutions of D6, E15 and/or E20 as defined above.

In some embodiments, a macrocycle-forming linker connects two amino acids separated by an intervening sequence of 3 or 6 amino acids. Preferably, the macrocycle-forming linker connects the amino acids in positions 3 and 7, 3 and 10, 6 and 10, 6 and 13, and 10 and 14 of the sequence (I).

In some preferred embodiment, the sequence (I) consists of:

(SEQ ID NO: 2)
$LKX_1QAX_2X_3YK\ X_4RFX_5X_6X_7R\ X_8ARX_9K$ in which:

$X_1$ is A or a cross-linked amino acid;
$X_2$ is D, a cross-linked amino acid or a neutral amino acid;
$X_3$ is I or a cross-linked amino acid;
$X_4$ is A or a cross-linked amino acid;
$X_5$ is Q or a cross-linked amino acid;
$X_6$ is A or a cross-linked amino acid;
$X_7$ is E or a neutral or basic amino acid;
$X_8$ is H or Q; and
$X_9$ is E or a neutral or basic amino acid;

providing that one pair of amino acids chosen from $X_1$ and $X_3$, $X_1$ and $X_4$, $X_2$ and $X_4$, $X_2$ and $X_5$, and $X_4$ and $X_6$ is cross-linked by the macrocycle-forming linker.

In a more preferred embodiment, each of $X_2$, $X_1$ and $X_9$ is neutral or basic amino acid.

In some embodiments, each amino acid connected by the macrocycle-forming linker (cross-linked amino acid) is a α,α-disubstituted amino acid, preferably comprising an α-methyl. The α,α-disubstituted amino acid can be any amino acid such as an alanine or another amino acid.

In some embodiments, the macro-cycle forming linker (L) is a $C_4$ to $C_{18}$ alkenylene, preferably a $C_8$ or $C_{11}$ alkenylene. In such embodiments, L results from the connection of the alkenyl side-chains of the cross-linking amino acids by olefin methatesis.

In some preferred embodiments, the cross-linking amino acids which generate L are α-methyl, α-alkenyl amino acids, each containing a $C_5$ alkenyl, preferably a 4'-pentenyl. The $C_5$ alkenyl, preferably a 4'-pentenyl, is advantageously in S configuration.

In other preferred embodiments, the cross-linking amino acids which generate L are α-methyl, α-alkenyl amino acids, wherein the first amino acid contains a $C_8$ alkenyl, preferably a 7'-octenyl, and the second amino acid contains a $C_5$ alkenyl, preferably a 4'-pentenyl. The $C_8$ alkenyl, preferably a 7'-octenyl, is advantageously in R configuration and the $C_5$ alkenyl, preferably a 4'-pentenyl, is advantageously in S configuration.

Such type of stapled peptides, known as all-hydrocarbon stapled alpha-helical peptides, are disclosed in Schafmeister et al. [3], Verdine and Hilinski. [4] and Kim et al. [5].

Other types of stapled peptides are known in the art such as those disclosed for example in WO 2014/138429. Such other stapled peptides which are within the skill of one in the art can be used in the invention. In particular a double hydrocarbon staple as well as multiple contiguous staples (recently called stitched peptide, [6]) could be used. Other cross-links stabilizing α-helical conformation could be also inserted in the sequence (I) such as lactam, disulfide, thio-ether, azobenzene, hydrazone, triazole, biphenyl, bis-triazoylyl, oxime, perfluoroaryl and carbamate.

In other embodiments, the peptide of the invention is a fusion or chimeric peptide further comprising an amino acid sequence (II) fused to the N- and/or C-terminus of the sequence (I). The length of the chimeric peptide is not critical to the invention as long as the peptide is functional. The sequence (I) is advantageously fused to a peptide moiety which increases the stability, bioavailability, bioactivity, cell-targeting and/or cell-penetration of the peptide, and/or allow its detection.

In a preferred embodiment, the peptide further comprises a cell-penetrating peptide sequence (CPP) fused to the N- and/or C-terminus, preferably the N-terminus of the sequence (I). The CPP sequence is fused to the sequence (I), directly or via a peptidic linker, preferably directly. CPP sequences are well-known in the art and many sequences which are within the skill of one in the art can be used in the present invention. For example, the CPP is a polyarginine sequence (R7, R9), a cationic peptide derived from HIV TAT protein transduction domain or an Antennapaedia peptide. A preferred CPP sequence is Antennapaedia peptide sequence SEQ ID NO: 3.

The invention encompasses peptides comprising or consisting of natural amino acids (20 gene-encoded amino acids in a L- and/or D-configuration) linked via a peptide bond as well as peptidomimetics of such protein where the amino acid(s) and/or peptide bond(s) have been replaced by functional analogues. The invention also encompasses modified peptides derived from the above peptides by introduction of any chemical modification into one or more amino acid residues, peptide bonds, N- and/or C-terminal ends of the protein/peptide, as long as the modified peptide is functional. These modifications which are introduced into the peptide by the conventional methods known to those skilled in the art, include, in a non-limiting manner: the substitution of a natural amino acid with a non-proteinogenic amino acid (D amino acid or amino acid analog); the modification of the peptide bond, in particular with a bond of the retro or retro-inverso type or a bond different from the peptide bond; the addition of a chemical group to the side chain or the end(s) of the peptide, in particular for coupling an agent of interest to the peptide of the invention. These modifications may be used to increase the stability, bioavailability or bioactivity of the peptide, or to label the peptide.

The peptide of the invention consists usually of up to 100 amino acids, preferably up to 50 or 40 amino acids.

In some embodiments, the peptide of the invention consists of the sequence (I).

In other embodiments, the peptide of the invention consists of the sequence (I) and (II), preferably the sequence (I) and a CPP sequence, as defined above.

In a more preferred embodiment, the peptide of the invention is selected from the group consisting of:

LKX$_1$QADX$_3$YKARFQAERHAREK (SEQ ID NO: 4)

LKAQAX$_2$IYKX$_4$RFQAERHAREK (SEQ ID NO: 5)

LKAQADIYKX$_4$RFQX$_6$ERHAREK (SEQ ID NO: 6)

RQIKIWFQNRRMKWKKLKAQADIYKX$_4$RFQX$_6$ERHAREK (SEQ ID NO: 7)

LKX$_1$QADIYKX$_4$RFQAERHAREK (SEQ ID NO: 8)

RQIKIWFQNRRMKWKKLKX$_1$QADIYKX$_4$RFQAERHAREK (SEQ ID NO: 9)

LKAQAX$_2$IYKARFX$_5$AERHAREK (SEQ ID NO: 10)

RQIKIWFQNRRMKWKKLKAQAX$_2$IYKARFX$_5$AERHAREK (SEQ ID NO: 11)

LKAQAX$_2$IYKARFX$_5$AQRHARQK (SEQ ID NO: 12)

RQIKIWFQNRRMKWKKLKAQAX$_2$IYKARFX$_5$AQRHARQK (SEQ ID NO: 13)

LKAQAX$_2$IYKARFX$_5$AX$_7$RHARX$_9$K, (SEQ ID NO: 14)
and

RQIKIWFQNRRMKWKKLKAQAX$_2$IYKARFX$_5$AX$_7$RHARX$_9$K, (SEQ ID NO: 15)

wherein the residues $X_1$, $X_2$, $X_3$, $X_4$, $X_5$ and $X_6$ are α,α-disubstituted amino acids, preferably comprising an α-methyl, and wherein the pair of residues $X_1$ and $X_3$, $X_2$ and $X_4$ and $X_4$ and $X_6$ of the sequences SEQ ID NO: 1 to 7 are connected by a $C_8$ alkenylene macrocycle forming linker and the pair of residues $X_1$ and $X_4$ and $X_2$ and $X_5$ of the sequences SEQ ID NO: 8 to 15 are connected by a $C_{11}$ alkenylene macrocycle forming linker; and wherein $X_7$ and $X_9$ represent Glutamic acid methyl ester (GluOMe).

Preferably, the peptide is any one of SEQ ID NO: 6, 7 and 10 to 15.

The invention relates also to a method of preparing the peptide of the invention, comprising the steps of:
a) synthesizing the amino acid sequence of the peptide of the invention, and
b) connecting two amino acids of the sequence obtained in a) through a macrocycle containing linker.

Step a) is performed by solid phase synthesis, preferably Fmoc solid-phase synthesis.

In a preferred embodiment, step a) comprises the incorporation of two α,α-disubstituted amino acids as defined above, in the amino acid sequence of the peptide, preferably separated by an intervening sequence of 3 or 6 amino acids. The α,α-disubstituted amino acids are preferably α-methyl, α-alkenyl amino acids. The α-methyl, α-alkenyl amino acids comprise preferably a $C_3$ to $C_{10}$ alkenyl.

In some more preferred embodiments, the α-methyl, α-alkenyl amino acids, preferably α-alkenyl alanines, each contain a $C_5$ alkenyl, preferably a 4'-pentenyl. The $C_5$ alkenyl, preferably a 4'-pentenyl, is advantageously in S configuration.

In other more preferred embodiments, the α-methyl, α-alkenyl amino acids, preferably α-alkenyl alanines, consist of a first amino acid containing a $C_8$ alkenyl, preferably a 7'-octenyl, and a second amino acid containing a $C_5$ alkenyl, preferably a 4'-pentenyl. The $C_8$ alkenyl, preferably a 7'-octenyl, is advantageously in R configuration and the $C_5$ alkenyl, preferably a 4'-pentenyl, is advantageously in S configuration.

In another preferred embodiment, step b) comprises, connecting the alkenyl side-chains of the α,α-disubstituted amino acids by olefin methatesis so as to form the macrocycle linker, preferably a $C_4$ to $C_{18}$ alkenylene, more preferably a $C_8$ or $C_{11}$ alkenylene.

The synthesis of such type of stapled peptides, known as all-hydrocarbon stapled alpha-helical peptides is disclosed in Schafmeister et al., [3], Verdine and Hilinski [4] and Kim et al. [5].

The invention relates also to a pharmaceutical composition comprising at least a peptide according to the invention and a pharmaceutically acceptable vehicle.

The pharmaceutical vehicles are those appropriate to the planned route of administration, which are well known in the art.

The composition of the invention comprises a therapeutically effective dose of peptide, sufficient to inhibit NF-κB signaling pathway and produce an anti-inflammatory and/or antitumoral effect in the individual to whom it is administered.

The effect of the composition according to the invention can be readily verified by various assays, which are known to the person of ordinary skill in the art such as those described in the examples of the present Application.

The effective dose is determined and adjusted depending on factors such as the composition used, the route of administration, the physical characteristics of the individual under consideration such as sex, age and weight, concurrent medication, and other factors, that those skilled in the medical arts will recognize.

In some embodiments, the composition further comprises at least an anti-inflammatory, immunomodulatory, and/or anticancer agent.

The invention provides also a peptide or pharmaceutical composition according to the invention for use as a medicament, in particular as anti-inflammatory or anticancer medicament.

The invention provides also a peptide or pharmaceutical composition according to the invention for use in the treatment a disease caused by hyperactivation and/or aberrant regulation of the NF-κB signaling pathway, in particular a cancer, anti-inflammatory disease or autoimmune disease.

The invention provides also a method for treating a disease caused by hyperactivation and/or aberrant regulation of the NF-κB signaling pathway, comprising: administering to an individual a therapeutically effective amount of the composition as described above.

In some embodiments, said cancer is a solid tumor or hematological cancer. Non-limitative examples of cancer include esophagus, stomach, colon, pancreas, melanoma, thyroid, lung, breast, kidney, bladder, uterus, ovary and prostate cancer; hepatocellular carcinomas, osteosarcomas, cylindromatose, neuroblastomas, glioblastomas, astrocytomas, colitis associated cancer, multiple myeloma and various types of leukemia and lymphomas such as diffuse large B-cell lymphoma, primary mediastinal B-cell lymphoma (PMBL), Hodgkin's lymphoma and MALT lymphoma. In some preferred embodiment said cancer is a lymphoma.

In some embodiments, said disease is an inflammatory disease, in particular an important inflammatory disease like asthma and chronic obstructive pulmonary disease (COPD) or inflammatory bowel disease (IBD).

In some embodiments, said disease is an autoimmune disease such as rheumatoid arthritis (RA) and diabetes or a disease associated with immune system such as transplant rejection.

In some embodiments, said disease or injury is a disease or injury linked to blood circulation trouble such as atherosclerosis or ischaemia reperfusion.

The composition of the present invention is generally administered according to known procedures, at dosages and for periods of time effective to induce an anti-inflammatory or anti-tumoral effect in the individual. The administration may be by injection or by oral, sublingual, intranasal, rectal or vaginal administration, inhalation, or transdermal application. The injection may be subcutaneous, intramuscular, intravenous, intraperitoneal, intradermal or else.

The practice of the present invention will employ, unless otherwise indicated, conventional techniques which are within the skill of the art. Such techniques are explained fully in the literature.

Figure 1B:
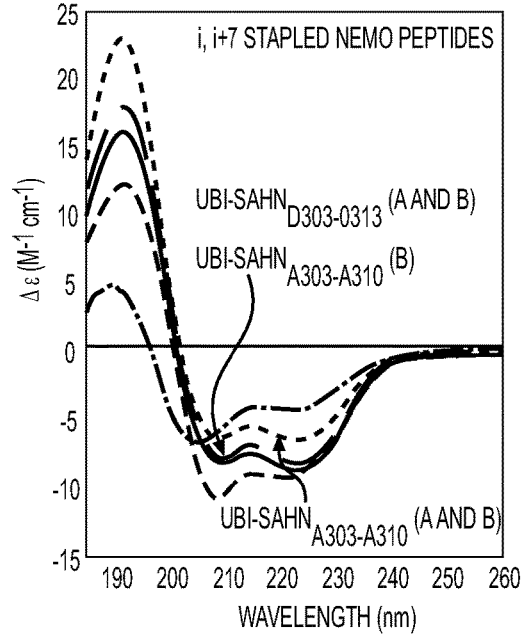
Figure 1C:
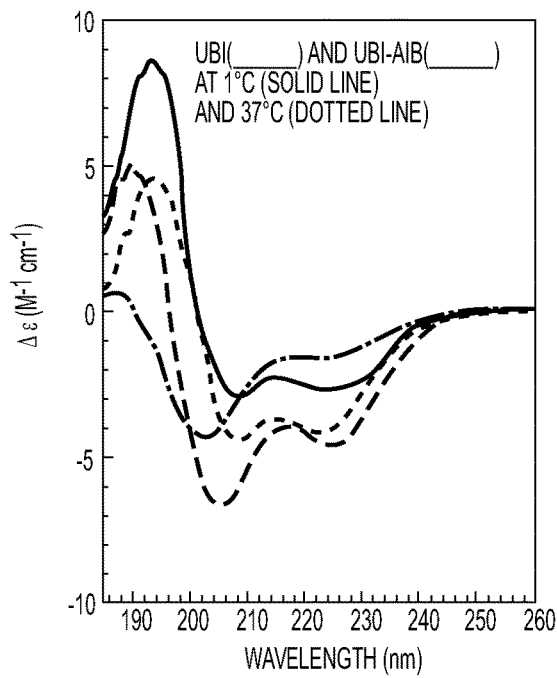
Figure 1D:
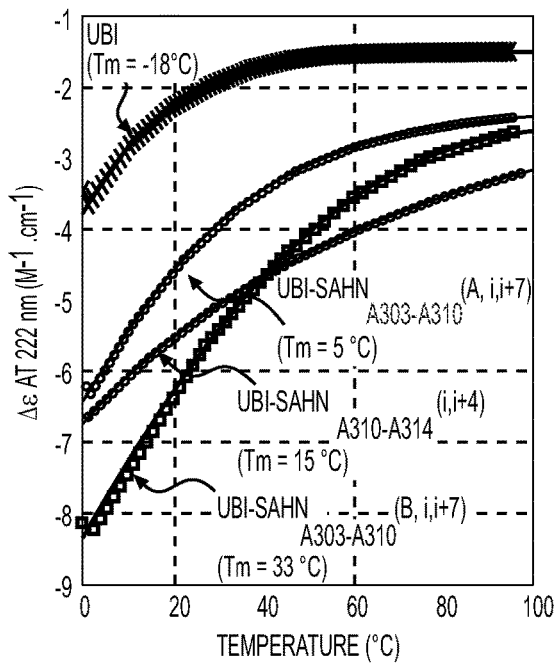

In addition to the above arrangements, the invention also comprises other arrangements, which will emerge from the description which follows, which refers to exemplary embodiments of the subject of the present invention, with reference to the attached drawings in which:

FIG. 1A-D: CD spectra and thermal stability of stapled and Aib NEMO peptides. All CD spectra were recorded at 1° C. and at the concentration of 50 μM in phosphate buffer at pH 7.0. In FIG. 1A and FIG. 1B, the reference spectra of the parental UBI peptide in TFE (corresponding to a fully α-helical monomeric structure) and phosphate buffer are indicated in dotted line and solid line, respectively. In FIG. 1C, CD spectra of UBI-AIB and UBI peptides were recorded at 37° C. and 1° C. To estimate percent α-helicity, the precise peptide concentrations were confirmed by amino acid analysis, the CD data converted to differential molar CD extinction coefficient per residue (Δε) and α-helicity calculated as described under Material and Methods. FIG. 1D, thermal denaturation profiles at a concentration of 30 μM of UBI i+4 UBI-SAHN$_{A310-A314}$ peptide and of two conformers (A and B) of i+7 UBI-SAHN$_{A303-A310}$ peptides as indicated.

Figure 2A:
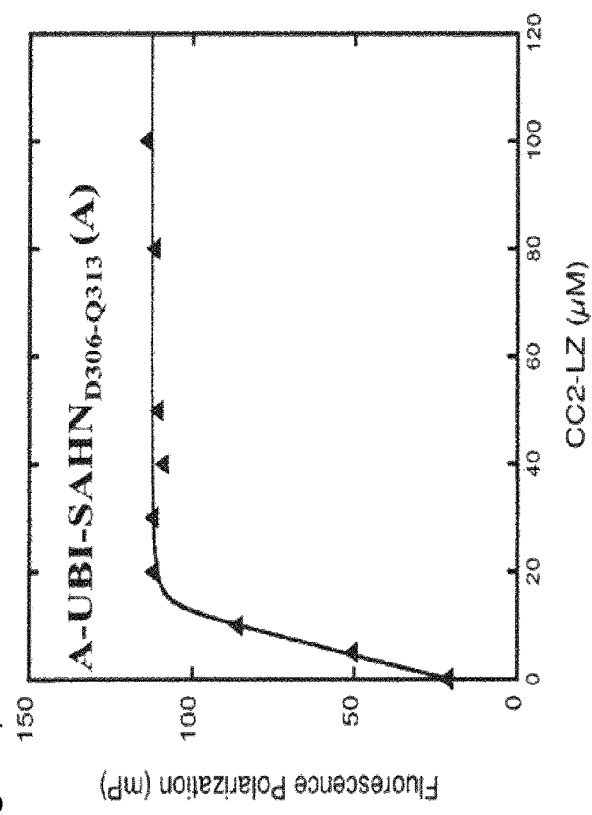
Figure 2B:
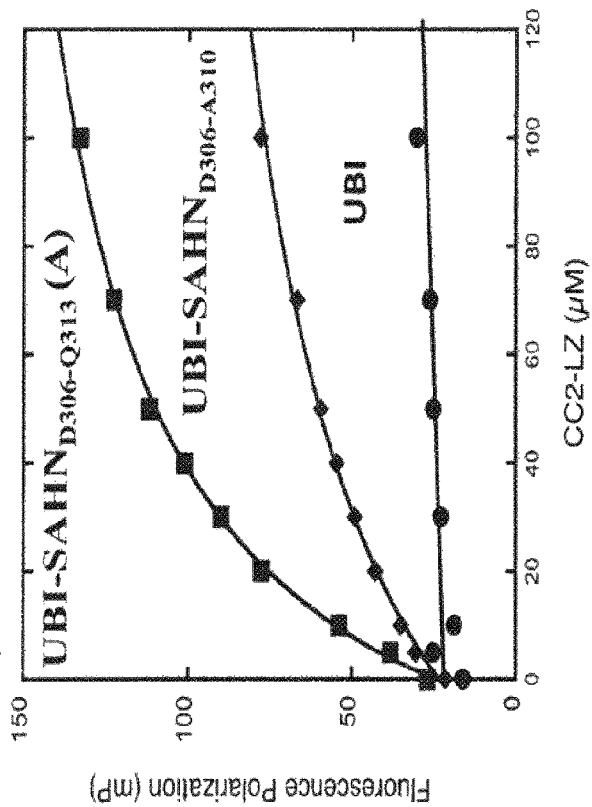

FIG. 2A-B: Titration curves of some NEMO stapled peptides with or without antennapedia FIG. 2A. Fluorescence polarization of the high affinity association of CC2-LZ with the A conformer (A) of the i,i+7 peptide, A-UBI-SAHN$_{D306-Q313}$, containing the antennapedia permeable sequence ($K_D$: 60±10 nM). FIG. 2B. Comparison of binding affinity to CC2-LZ between antennapedia-free i+4 and i+7 stapled peptides and UBI. The A conformer of UBI-SAHN$_{D306-Q313}$ (staple i+7) shows better affinity with a $K_D$ of 34±61.1M compared to the UBI-SAHN$_{D306-A310}$ i+4 stapled peptide ($K_D$ of 85±15 μM).

FIG. 3A-C: NF-κB inhibition of NEMO stapled peptides in pre-B lymphocytes with and without LPS stimulation. FIG. 3A. Inhibition activity of antennapedia-free stapled peptides at 10 μM as indicated. A-UBI was shown as internal positive control. FIG. 3B. Inhibition activity and IC$_{50}$ value of the A-UBI reference peptide. FIG. 3C. Inhibition activity and IC$_{50}$ value of the i,i+7 stapled peptide, A-UBI-SAHN$_{D306-Q313}$ (A), containing the antennapedia sequence. Peptides (10 μM) were incubated 2 h at 37° C., 5% $CO_2$ with 70Z3C3 cells, lysed and β-galactosidase activity read on a luminometer.

FIG. 4A-D: Cellular uptake of stapled peptides by FACS.

Figure 4A:
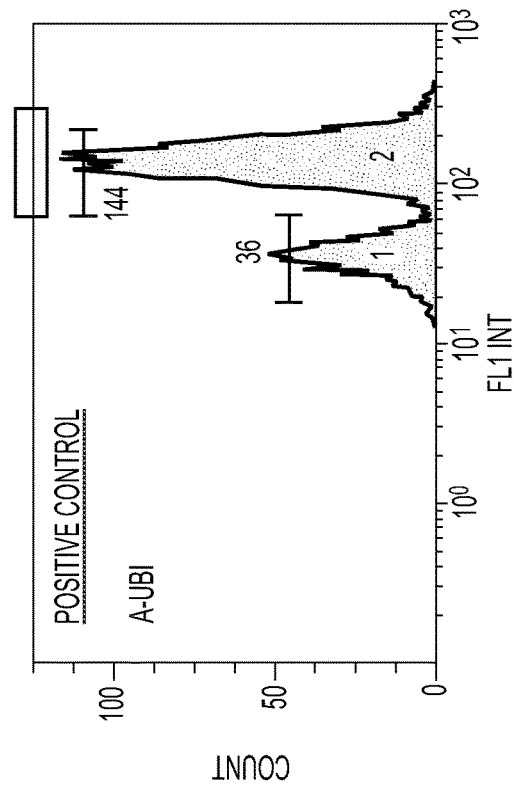
Figure 4B:
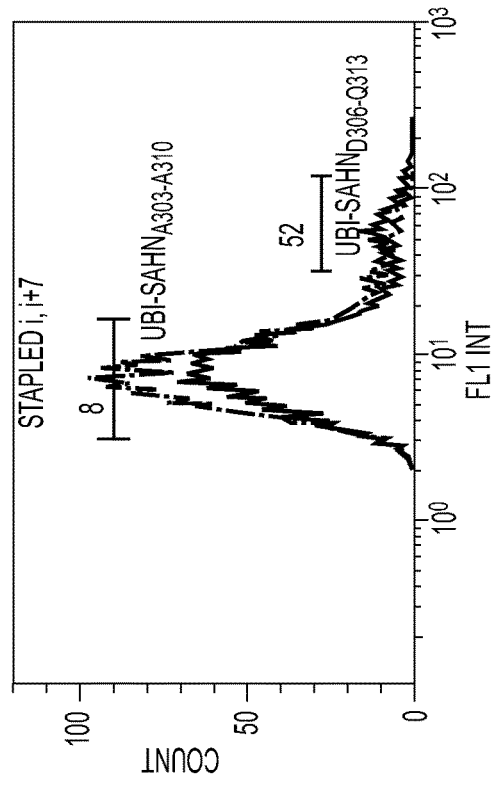
Figure 4C:
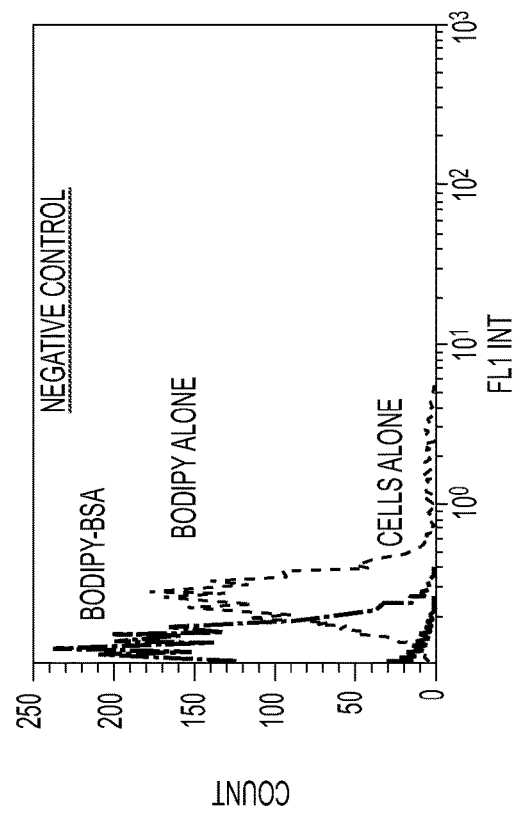
Figure 4D:
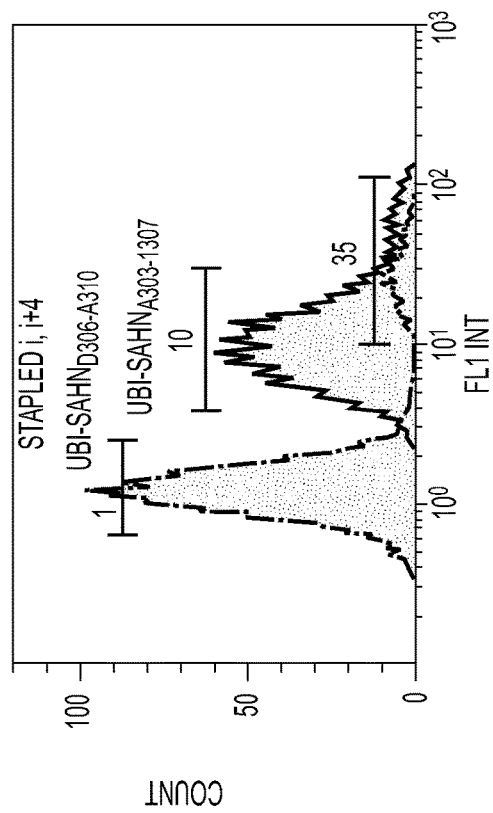

FIG. 4A. Cellular uptake of negative controls corresponding to untreated cells or cells incubated with BODIPY® alone or BODIPY®-BSA. FIG. 4B. Cellular uptake of positive control corresponding to the parental A-UBI containing antennapedia. FIG. 4C. Cellular uptake of some i,i+4 stapled peptides as indicated. FIG. 4D. Cellular uptake of some i,i+7 stapled peptides as indicated.

Figure 5:
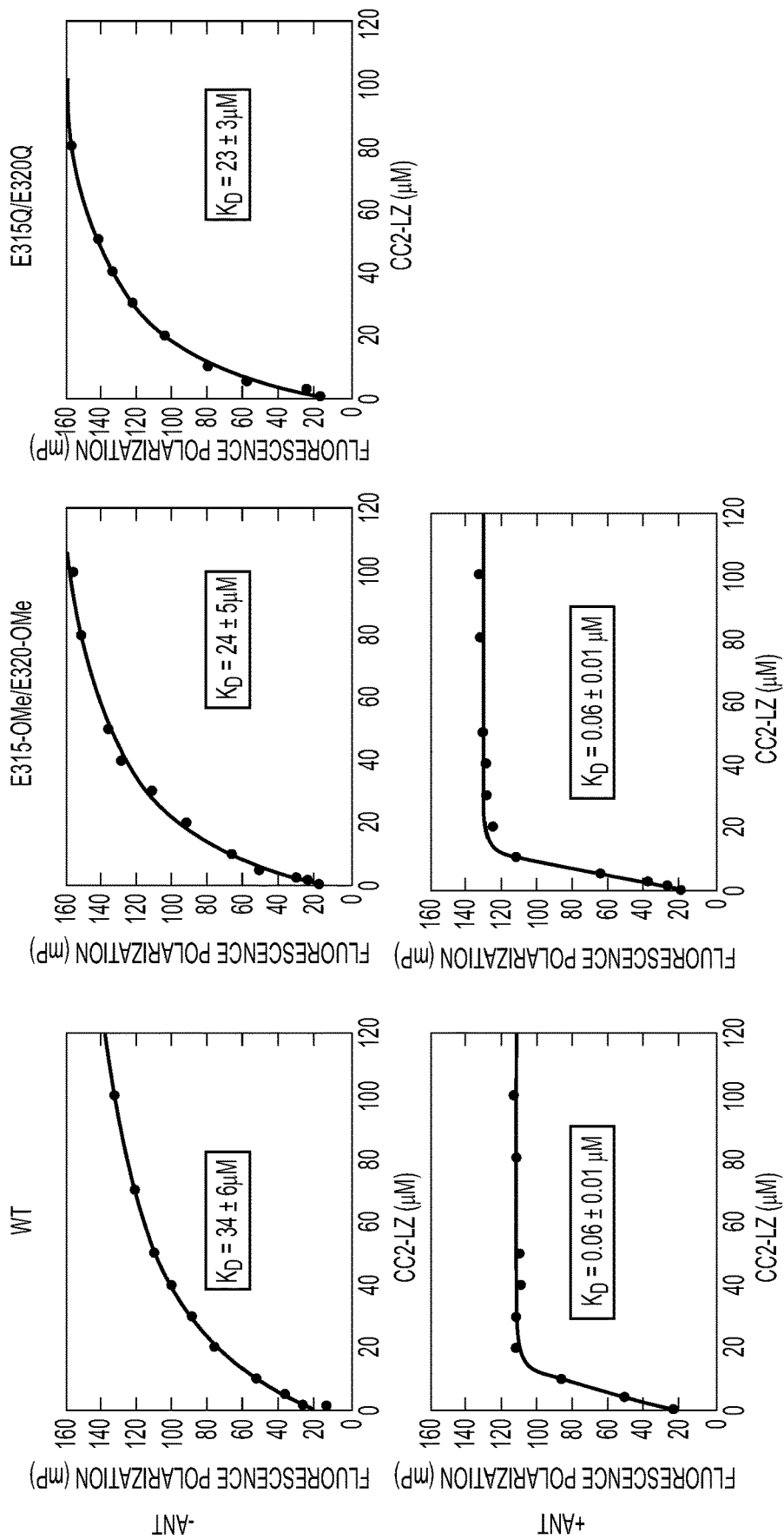

FIG. 5: Binding affinity of UBI-SAHN$_{D306-Q313}$ Q/Q and UBI-SAHN$_{D306-Q313}$ OMe with or without antennapedia (Ant).

Figure 6:
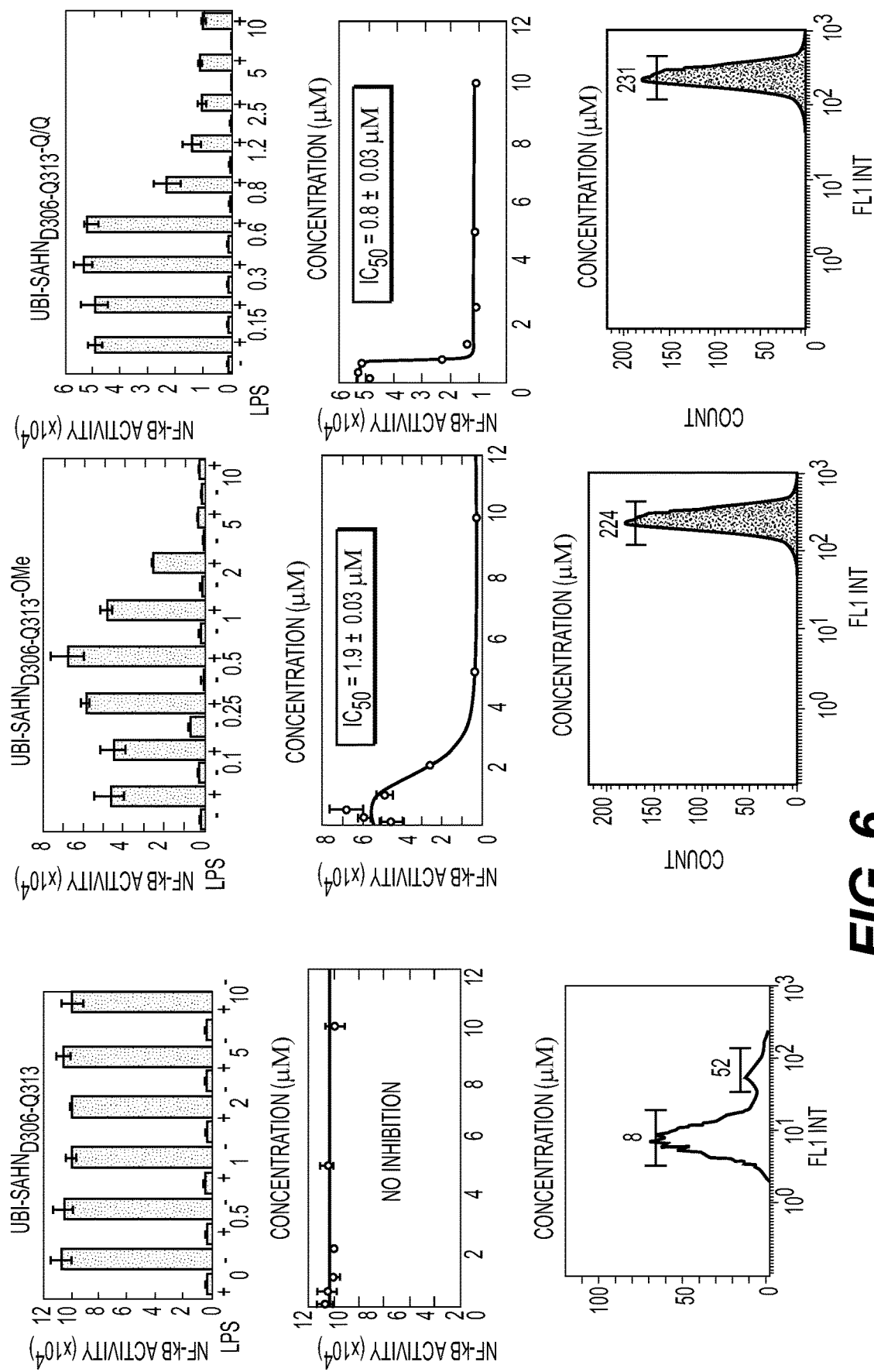

FIG. 6: Inhibition activity and cellular uptake of UBI-SAHN$_{D306-Q313}$ derived peptides devoid of antennapedia.

Figure 7:
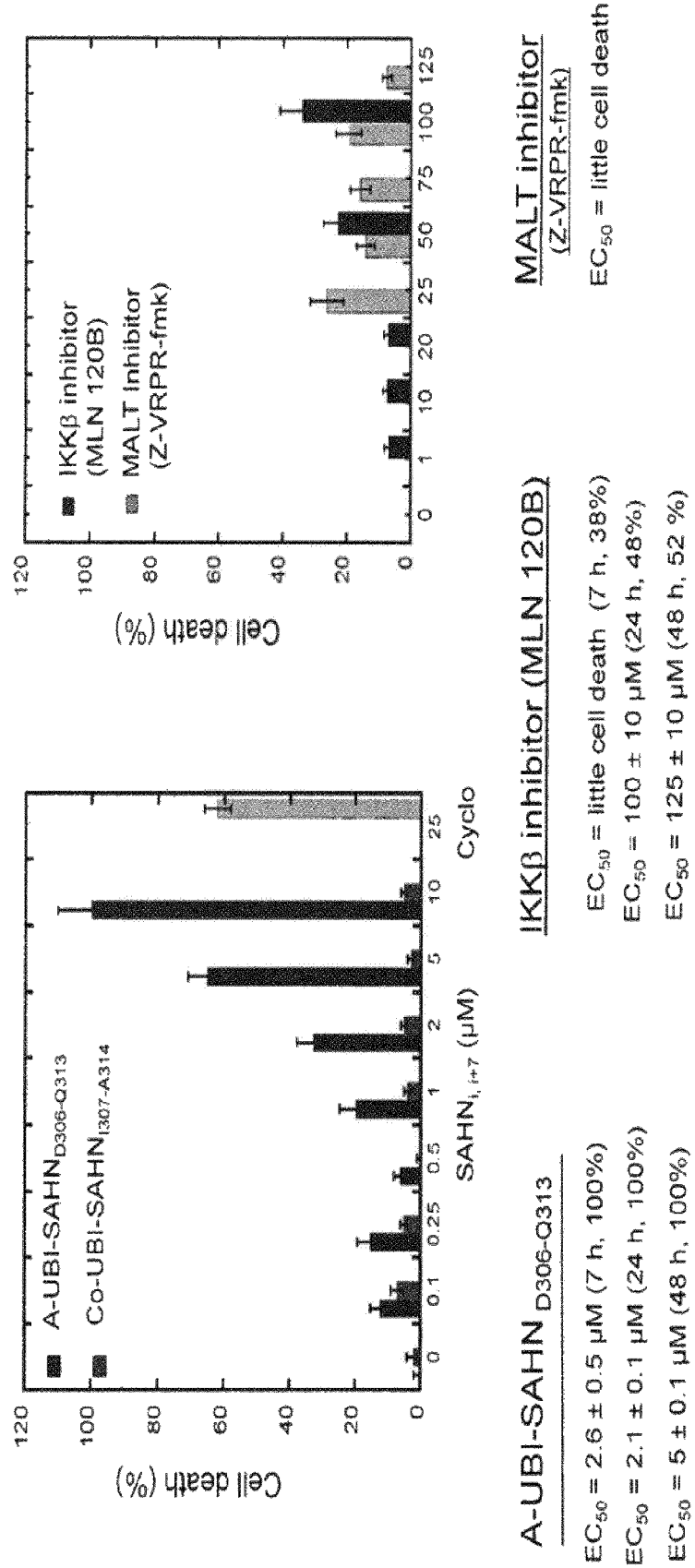

FIG. 7: Cell death assay with MALT1-dependent ABC-DLBCL, OCY-Ly3 (NF-κB ↗) cells treated with A-UBI-SAHN$_{D306-Q313}$, IKKβ inhibitor (MLN 120B) or MALT inhibitor (Z-VRPR-fink).

Figure 8:
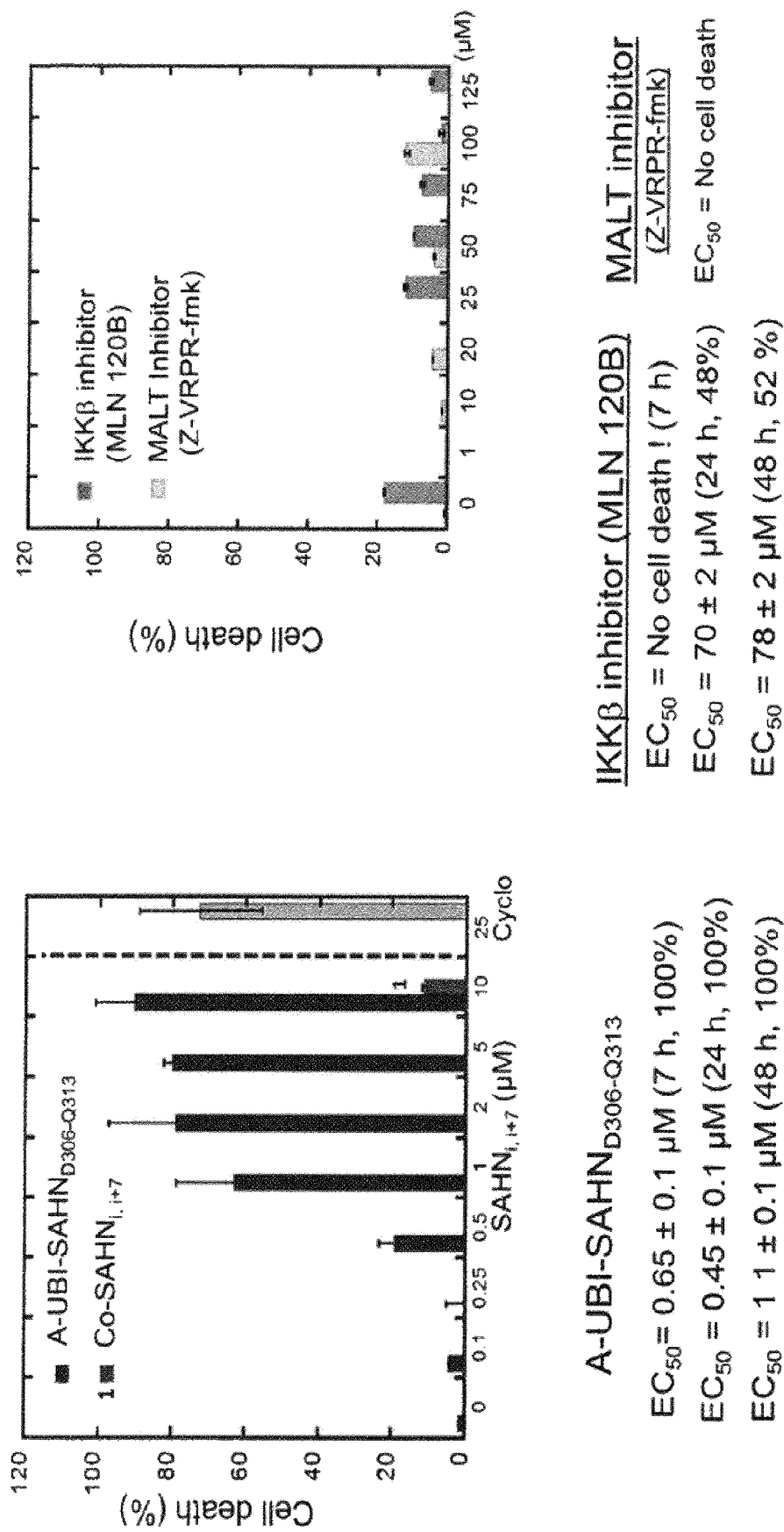

FIG. 8: Cell death assay with MALT1-independent ABC-DLBCL, HLY-1 (NF-κB ↗) cells treated with A-UBI-SAHN$_{D306-Q313}$, IKKβ inhibitor (MLN 120B) or MALT inhibitor (Z-VRPR-fmk).

Figure 9:
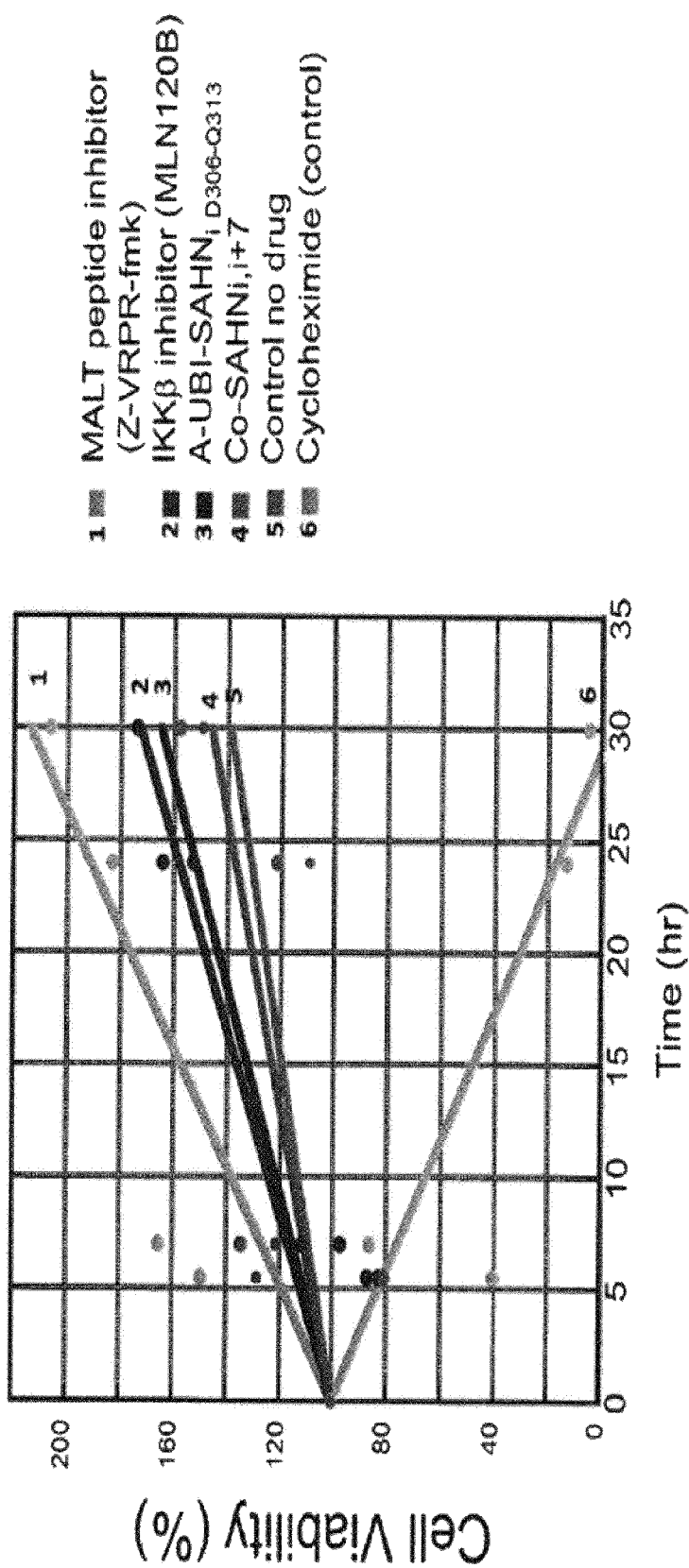

FIG. 9: Cell death assay with GCB-DLBCL cells, OCY-Ly7 (NF-κB ↘) treated with A-UBI-SAHN$_{D306-Q313}$, IKKβ inhibitor (MLN 120B) or MALT inhibitor (Z-VRPR-fmk).

Figure 10A:
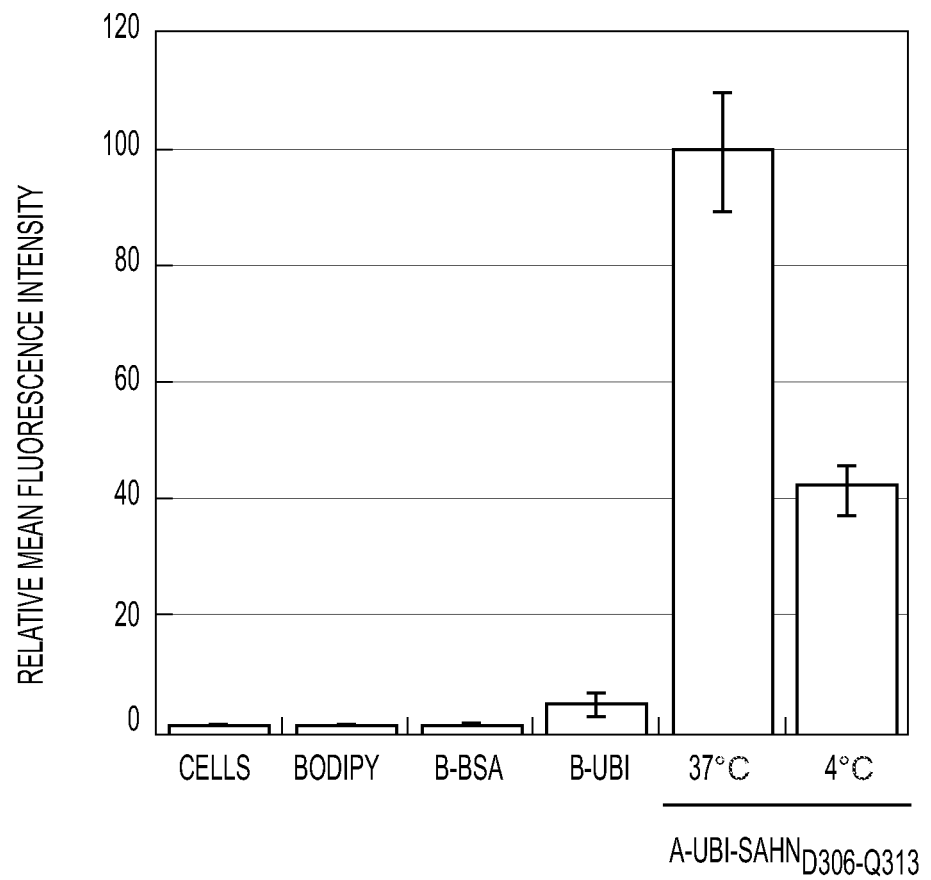
Figure 10B:
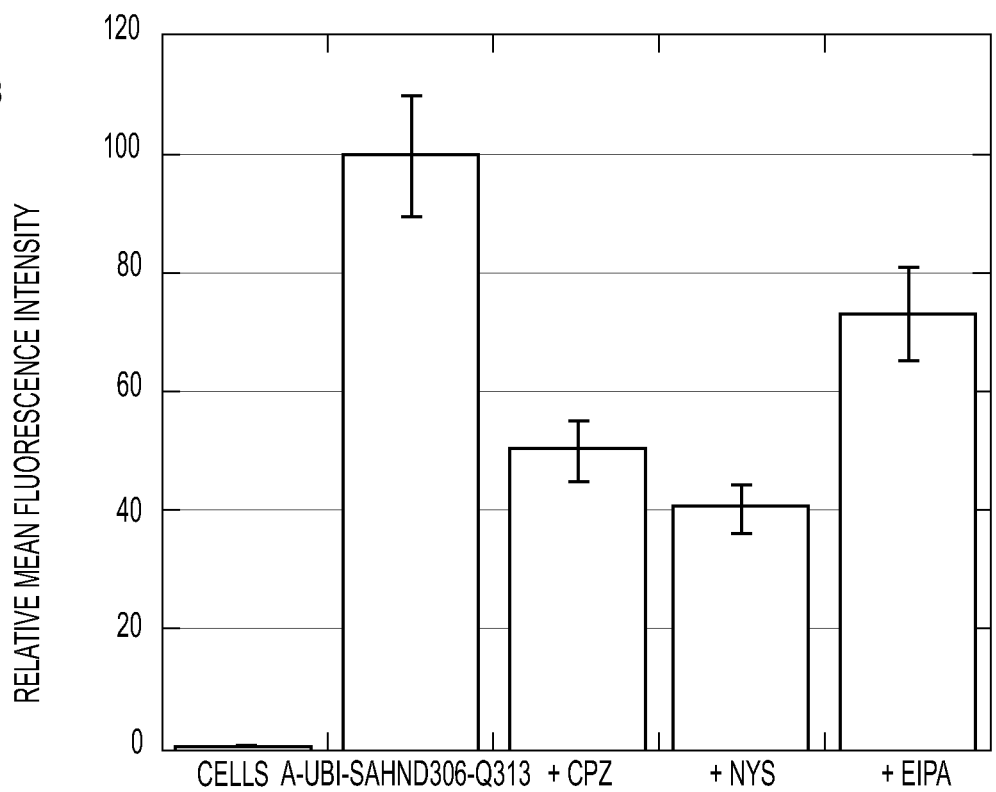

FIG. 10A-B: Cellular internalization mechanisms of the most potent NEMO stapled inhibitor (A-UBI-SAHN$_{D306-Q313}$)

(FIG. 10A) Energy dependent cellular uptake of A-UBI-SAHN$_{D306-Q13}$. Mean fluorescence intensity relative to the highest intensity with A-UBI-SAHN$_{D306-Q13}$ is shown as judged by flow cytometer analysis. The relative cellular internalization efficiency at the lowered temperature (4° C.) was compared with that at 37° C. The bodipy fluorophore, bodipy-labeled BSA (B-BSA) and UBI (B-UBI) which are impermeant to the cell membrane at 37° C. serve as negative controls.

(FIG. 10B) Cellular uptake of A-UBI-SAHN$_{D306-Q313}$ into the cells pre-treated with endocytosis inhibitors. CPZ, chlorpromazine (inhibitor of clathrin-mediated endocytosis); NYS, nystatin (inhibitor of caveolin-mediated endocytosis); EIPA, 5-(N-ethyl-N-isopropyl) amiloride (inhibitor of macropinocytosis). Each bar represents the average of two independent experiments.

Figure 11A:
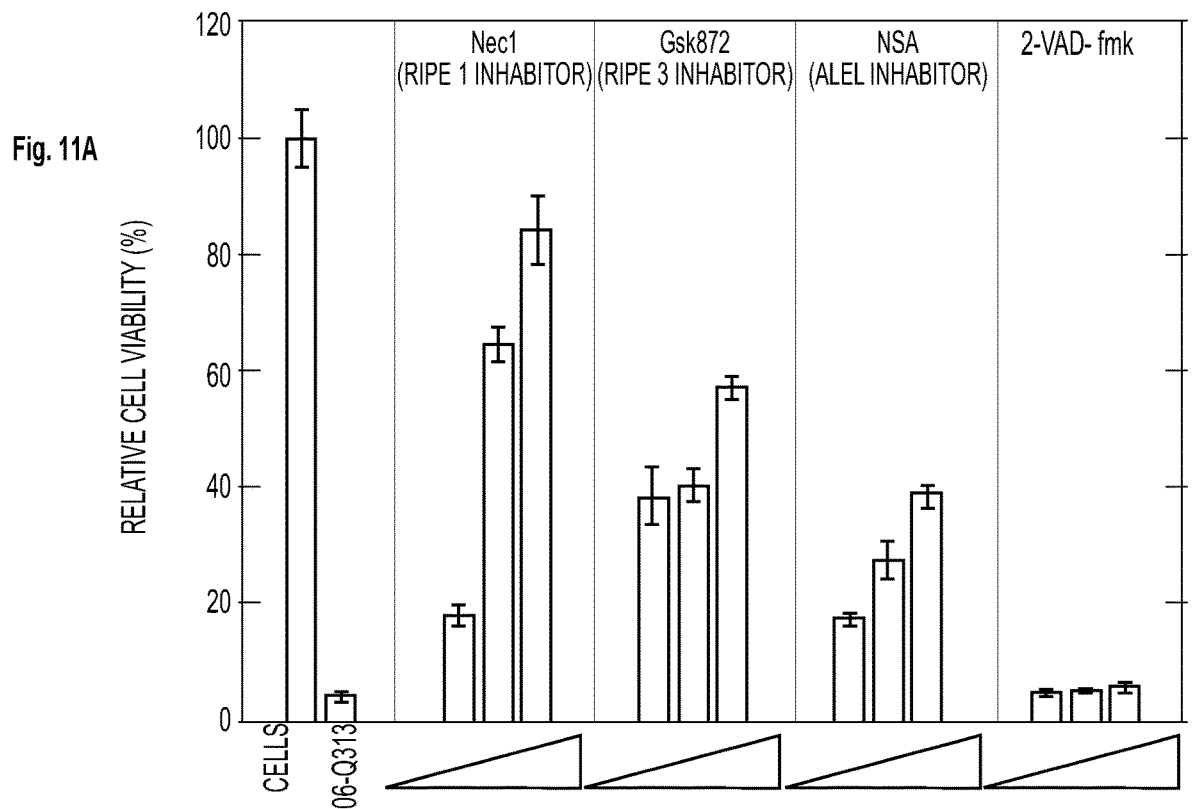
Figure 11B:
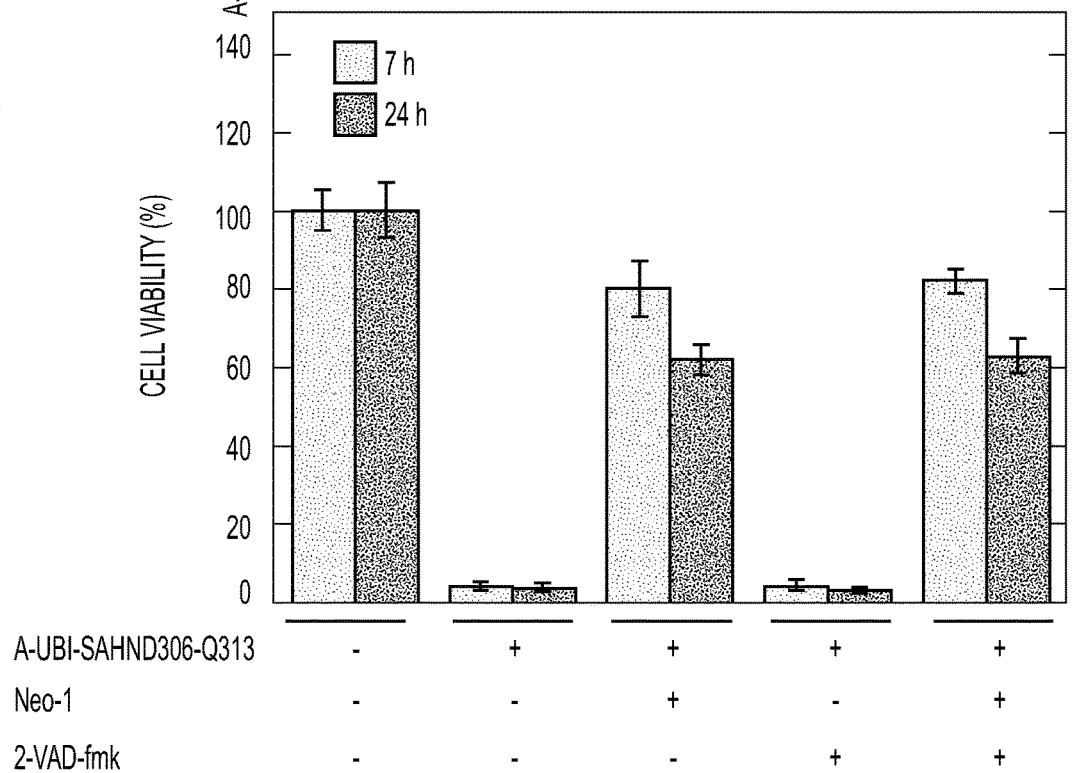

FIG. 11A-B: Protection of cell death induced-NEMO stapled inhibitor by apoptosis and necroptosis inhibitors (FIG. 11A) DLBLC cells (OCI-Ly3) were first pre-treated with different doses of necroptosis inhibitors, Nec-1, GSK872 or NSA, and the pan caspase inhibitor Z-VAD-fmk before incubation for 7 h with A-UBI-SAHN$_{D306-Q313}$. Relative cell viability was then assessed using the CellTiter-Blue assay (see Materials and Methods for further details).

(FIG. 11B) Effect of incubation time of RIPK1 (Nec-1) and of pan caspase (Z-VAD-fmk) inhibitors on the induction of DLBCL cell death (OCI-Ly3). A-UBI-SAHN$_{D306-Q313}$ was incubated with 100 μM of Nec-1 alone, 100 μM of Z-VAD-fmk alone or together for 7 h and 24 h. Cells with and without peptide were used as control.

Figure 12:
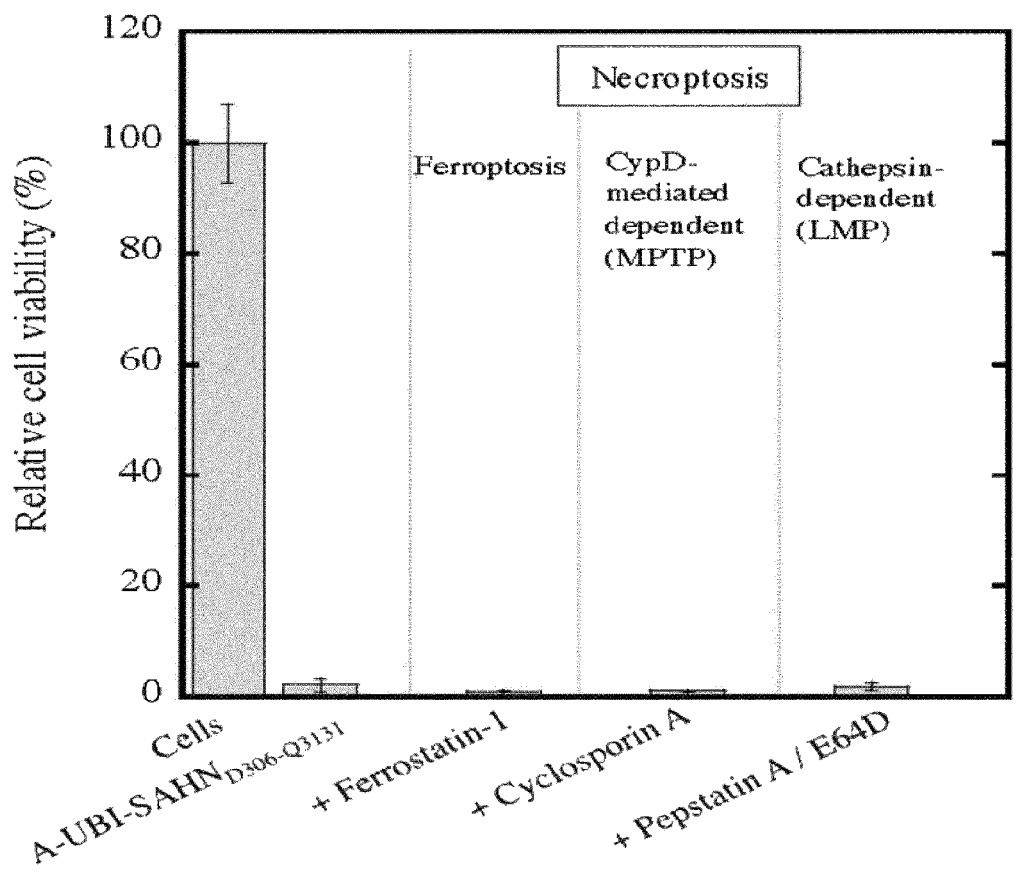

FIG. 12: Analysis of different forms of necroptotic pathways involved in DLBCL cell-death induced by NEMO stapled peptide Well-established inhibitors of different necroptotic pathways, Ferrostatin-1 (inhibitor of ferroptosis), cyclosporin A (inhibitor of CypD-dependent necroptosis) and pepstatin A and E64D mixture (inhibitor of cathepsin dependent necroptosis), were pre-treated with DLBCL cells (OCI-Ly3) each at 10 μM before incubating with the NEMO stapled peptide (A-UBI-SAHN$_{D306-Q313}$) for 7 h. Cell viability was then measured as indicated in FIG. 11. Abbreviations used are: MPTP, mitochondrial premeability transition pore; LMP, lysosomal membrane permeability.

Figure 13A:
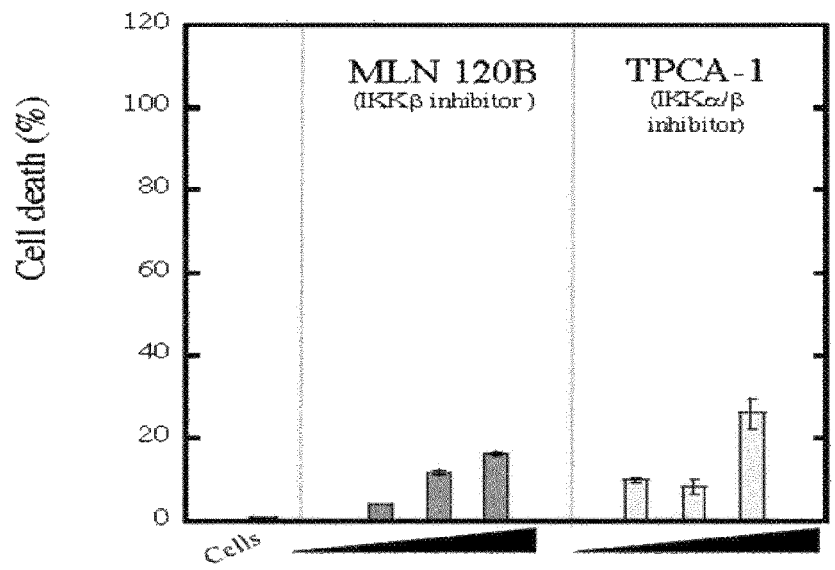
Figure 13B:
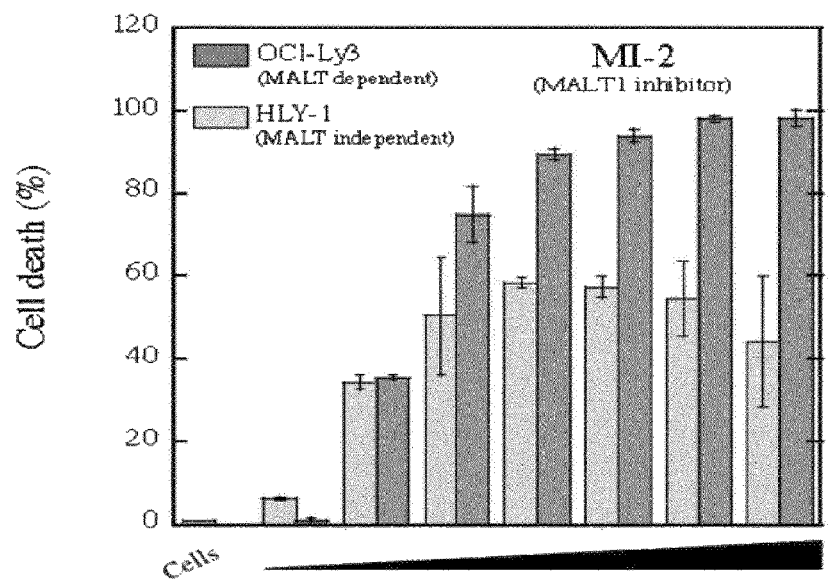

FIG. 13A-B: A comparative study of cell death induced by IKKα/β and MALT1 inhibitors (FIG. 13A) A dose dependence ranging from 0 to 50 μM of either IKKβ (MLN120B) or IKKα/β (TPCA-1) inhibitors was incubated with DLBCL cells (OCI-Ly3) for 7 h. Relative cell death (%) was determined using cell viability assay as indicated in FIG. 10.

(FIG. 13B) An increasing concentration of MI-2 (MALT1 inhibitor) from 0 to 20 μM was incubated either with MALT dependent (OCI-Ly3) or MALT independent (HLY1) DLBCL cell lines for 7 h, before measuring the effect on cell death (%).

There will now be described by way of example a specific mode contemplated by the Inventors. In the following description numerous specific details are set forth in order to provide a thorough understanding. It will be apparent however, to one skilled in the art, that the present invention may be practiced without limitation to these specific details. In other instances, well known methods and structures have not been described so as not to unnecessarily obscure the description.

EXAMPLE 1: MATERIAL AND METHODS

Cell Lines, Antibodies and Reagents

The stable cell line of pre-B lymphocyte 70Z3-C3 cells expressing the lacZ reporter gene under the control of NF-κB was previously described[7]. OCI-Ly3 (ABC-DLBCL, MALT1 dependent) and OCI-Ly7 (GCB-DLBCL). U2932 (ABC-DLBCL, MALT1 independent) were purchased from DSMZ (Deutsche Sammlung von Mikroorganismen and Zellkulturen) and HLY1 (ABC-DLBCL, MALT1 independent). Jurkat T-cells were obtained after transduction of lentiviruses containing a NF-κB reporter luciferase gene as previously described [1]. All cell lines were grown in RPMI 1640 medium supplemented with 10% FBS, 10 μg/ml of streptomycin, 10 U/ml of penicillin and kept at 37° C., in a 5% $CO_2$ humidified incubator. 0.05 mM of β-mercaptoethanol was added for 70Z3-C3. Primary and secondary antibodies were as following: polyclonal rabbit anti NF-κB p65, (sc-372, Santa Cruz Biotechnology, Inc) Alexa-488 coupled goat anti-rabbit $IgG_1$ (Invitrogen)

Structural Model of the Human CC2-LZ Complex with a M1 or K63 Diubiquitin Chain

The human CC2-LZ complex with either a M1- or K63 di-ubiquitin chain was built by homology modeling from our recent crystal structure of the human CC2-LZ apoform at 2.27 Å resolution (PDB ID: 4BWN) and using the atomic crystal coordinates from the mouse complex with a linear (PDB: 2ZV0) or K63 diubiquitin chain (PDB: 3JSV). During docking calculations, no clashes were observed and only minor energy minimization was performed to generate the two models.

Design of NEMO Stapled Peptides

Based on the two structural models of the human CC2-LZ complex with a M1- or K63-diubiquitin chain, the insertion of all-hydrocarbon i,i+4 and i,i+7 staples into the UBI-derived peptide spanning residues 301-321 (human sequence) was rationally designed. The rational for the design was the following: first, the insertion of hydrocarbon constraint could not perturb the dimeric interface of the coiled-coil CC2-LZ/NOA/UBAN domain. Accordingly, no non-natural α,α-disubstituted aminoacid bearing olefin tethers was substituted for natural amino acid at positions a, d, e and g of the coiled-coil structure. Second, the insertion of i,i+4 and i,i+7 staples which could alter by steric clashes the binding of the distal ubiquitin and the ubiquitin linkage was favored, since previous mutagenesis studies showed that it represents the hot-spot segment of the CC2-LZ:di-ubiquitin interaction.

Stapled Peptide Synthesis

The synthesis protocol of all stapled peptides was derived from the general method published by G. L. Verdine [4] [5]. The main differences lie in the use of argon bubbling instead of nitrogen during the ring closing metathesis reaction. Experimental masses and specific protocol details for each stapled peptide are shown in Tables I and II.

Briefly, synthesis was carried out on an ABI 433 synthesizer (Applied Biosystems, Foster City, CA, USA) equipped with a conductivity flow cell to monitor Fmoc deprotection. Fmoc Amide resin (100 μmole, capacity 0.67 mmol/g) and standard Fmoc amino acids (side-protected as followed: tBu for aspartic acid, glutamic acid, serine, threonine and tyrosine; trityl for cysteine, histidine, asparagine and glutamine; Boc for lysine and tryptophane; 2,2,4,6,7-pentamethyl-dihydrobenzofuran-5-sulfonyl for arginine) were purchased from Applied Biosystems. (S)-2-(((9H-Fluoren-9-yl) methoxy)carbonylamino)-2-methylhept-6-enoic-acid/(S)—N-Fmoc-2-(4'-pentenyl) alanine/S5 and (R)-2-(((9H-Fluoren-9-yl)methoxy)carbonylamino)-2-methyldec-9-enoic acid/(R)—N-Fmoc-2-(7'-octenyl) alanine/R8 were obtained from O Keanos Tech., Beijing, China. Standard Fmoc-amino acids were activated with HATU/DIPEA (1-[Bis(dimethylamino)methylene]-1H-1,2,3-triazolo[4,5-b]pyridinium 3-oxid hexafluorophosphate/N,N-diisopropylethylamine) and single coupled with an eightfold molar excess with regard to the resin. Coupling of the olefinic building blocks was manually performed using an extra-synthesizer device. Both coupling reagents, as well as N-methyl pyrrolidone (NMP), were purchased from Applied Biosystems. Piperidine was purchased from Sigma-Aldrich (St Louis, MO, USA).

Manual Coupling of Olefin Building Blocks

S5 and R8 manual coupling steps were performed by interrupting automatic synthesis after Fmoc deprotection of the previous amino acid, as regards to the ongoing synthesis, and manual NMP-washing. The resin was washed again 3 times with Dimethylformamide (DMF) in a sintered glass filtering tube and drained. 0.2 mmoles HATU (2 eq) in 1.5 ml DMF was added on 0.25 mmoles (2,5 eq) S5 or R8 and mixed by vortex 5 min. DIEA (0.5 mmole; 5 eq) is added to this solution, 1 min before addition of the whole mixture on the resin. Mixing was maintained during two hours by gently bubbling Argon through the filter. Coupling completeness was visually checked using the colorimetric Kaiser test. Resin was washed with DMF and NMP before resumption of the automatic synthesis. ⅔ of the resin was saved before the coupling step of N-terminus cysteine. As a result, coupling of N-terminus cysteine was achieved on approximately ⅓ resin (≈33 μmoles).

N-Terminus Acetylation

After the final deblock and NMP-washing steps, the resin was soaked in a sintered glass filtering tube with a mixture of DIEA 20% in DMF, then washed three times with DMF. Specific N-terminal acetylation was achieved manually by stirring the peptide resin for 30 min in an excess of an acetylation cocktail containing 10% acetic anhydride in DMF. This operation was repeated twice before final washing with DMF and MeOH. Resin samples were saved in order to check the synthesis yields before stapling.

Olefin Metathesis

The resin was placed in a sintered glass filtering tube, washed with DCM, 3×1 min then with dry 1,2-dichoroethane (DCE) 3×1 min and gently mixed by argon bubbling in 1 ml fresh mixture of Grubbs' first generation catalyst (5 μmoles) in 1 ml DCE for 2 hours at ambient temperature. DCE was regularly added to counterbalance evaporation. The resin was washed with DCE before repeat of the treatment and finally washed with DCE (3×1 min) then with DCM (3×1 min). A sample cleavage was performed to check by RP-HPLC the completion of ring-closing olefin metathesis. As a result, completion was achieved for nearly all peptides (a supplementary two-steps protocol was necessary to minimize $D306R_8$-$Q313S_5$ unstapled peptide). Grubb's catalyst and DCE were purchased from Sigma.

Cleavage from the Resin

Cleavage from the solid support and deprotection of the amino acid side chains were accomplished in one step by treatment with 94:1:2.5:2.5 mixture of TFA (Applied Biosystems), triisopropylsilane, ethanedithiol, (Sigma-Aldrich) and water for 2 h30 at room temperature. After filtration of the resin, the cleavage mixture was poured into ice-cold diethyl ether. The precipitate was recovered by centrifugation, washed three times with cold diethyl ether, dried, dissolved in aqueous TFA and freeze dried. Crudes were solubilized before analysis or purification either in aqueous TFA 0.08% w/o acetonitrile or in aqueous formic acid 10% (Tables I and II). BODIPY® labeled Peptides were derivatized using N-ethyl maleimide (Sigma-Aldrich), 2 up to 4.5 equivalents or BODIPY® FL N-(2-aminoethyl)maleimide, 1.1 up to 1.4 equivalents, in a 0.1M phosphate buffer, pH 6 or 7.2. Derivatizations were performed either on the crude product or on the purified free-thiol peptide (Tables I and II)).

Purification of Stapled Peptides

Free-thiol, NEM and BODIPY® peptides were purified on reverse phase either by MPLC (AP-100/200 flash, Armen Instrument, Saint Ave, France) using a preparative column (26×313 mm) packed with 100 Å 20 μm C18 Nucleoprep packing (Macherey & Nagel GmbH & Co, Duren, Germany), by applying a linear gradient of solvent B (mixture of MeCN and solvent A, 8:2 v/v) in solvent A (0.08% aqueous TFA, pH 2 or 50 mM ammonium acetate, pH 6.5) over 60 min at a 20 ml/min flow rate, or by HPLC (Perkin-Elmer Series 200 HPLC system) using a Kromasil® 300 Å 5 μm C18 10×250 mm column (AIT, France) by applying a linear gradient of MeCN in solvent A over 20 min at a 6 ml/min flow rate. The purification was monitored at 214 or 230 nm. Suitable fractions were pooled and lyophilised. The final net peptide content was determined by quantitative amino acid analysis (Tables I and II).

HPLC Analysis

Analysis of crude mixtures and purity control of the final peptides were performed by RP-HPLC on an Agilent (Santa Clara, CA, USA) 1100 Series liquid chromatograph and monitored with a photodiode array detector by absorbance at 230 nm, by applying a linear gradient of acetonitrile in aqueous solvent A over 20 min at a 0.35 ml/min flow rate on a Symmetry300 C18 3.5 μm (Waters, Manchester, UK) or an Aeris PEPTIDE 3.6 μm XB-C18 analytical (2.1×100 mm) column (Phenomenex, Le Pecq, France) (Tab). LC-MS data were obtained using a Waters Alliance 2695 system comprising a 2487 dual absorbance detector and coupled with a TOF-MS detector (Waters Q-TOF Micro) with the following eluents: A: water containing 0.05 formic acid and 0.04% TFA, B: solution of acetonitrile containing 0.025% formic acid. Data acquisition and process are described below.

Electrospray Ionisation Mass Spectrometry Analysis.

Mass spectrometry was carried out on a quadrupole-TOF Micro mass spectrometer (Waters) equipped with a Z-spray API source and calibrated with a phosphoric acid calibration solution. Data were acquired in positive-ion mode by scanning over the m/z range 150-2000. The raw multi-charged spectra were processed using the MaxEnt 1 deconvolution algorithm embedded in the Masslynx software. Data were consistent with the expected masses (Tables I and II).

Cis/Trans Stereoisomerism of the i, i+7 NEMO Stapled Peptides

For all i+7 NEMO stapled peptides generated, two CIS/TRANS stereoisomers with a ratio of 64%/36%, 37%/63% and 26%/74% for 306-313, 303-310 and 307-314, respectively, were observed. Each isomer arbitrarily denoted A and B could be isolated and purified by HPLC and assessed for their ability to bind the NEMO NOA domain (also called CC2-LZ/UBAN/NUB) and inhibit the NF-κB pathway in cell. The nature of isomerism was confirmed by NMR analysis on the stapled $D306R_8$-$Q313S_5$ peptide. Significantly, these isomeric forms were never observed with the i,i+4 stapled peptides.

Design and Synthesis of NEMO Peptide Containing α-Amino-Isobutyric Acid (Aib) Residues It was previously shown that insertion of the Aib constrained residues promotes formation of α-helix structure, especially when Aib content does not exceed 40% of the peptide sequence [8]. In line with this, an UBI-derived peptide denoted UBI-AIB was synthesized, in which all Ala residues representing 23.8% of the total sequence were substituted with Aib residues (Table III). The peptide synthesis was performed using Fmoc standard methods as previously described.

CD Spectroscopy and Thermodynamic Analysis

CD measurements were performed on an Aviv215 spectropolarimeter (Aviv Instruments, Lakewook, NJ) with dissolved NEMO peptides in 10 mM sodium phosphate buffer at pH 7.0 or in 100% trifluoroethanol (TFE). The CD spectrum of UBI recorded in 100% TFE and at 1° C. was used as internal control to assess the maximum helicity for a given peptide. The CD spectrum under these experimental conditions was similar to that of published tables for peptide reference CD spectra with a fully α-helical structure [9], indicating the high propensity of UBI to adopt a 100% α-helical conformation. All CD spectra were monitored and deconvoluted as previously described in Grubisha et al. [10], except that UBI CD spectrum in 100% TFE and at 1° C. was taken as reference CD spectrum for a fully α-helical structure.

Temperature-induced denaturation experiments were performed by measuring the ellipticity at 222 nm from 1° C. to 95° C. in 1° C. steps, at a rate of 1° C./min, with a 2 nm bandwidth. Thermodynamic parameters including the melting temperature ($T_m$) and the van't Hoff enthalpy change at the melting temperature ($\Delta H_m$) were determined by fitting the denaturation curves with the Gibbs-Helmholtz equation as described elsewhere [11], [10]. The heat capacity change ($\Delta Cp$) was assumed to be 0 as judged by $\Delta H_m$ which yielded similar values within 10% at two independent peptide concentrations (30 and 300 µM). The ellipticity was converted to differential extinction coefficient $\Delta\varepsilon$ ($M^{-1} \cdot cm^{-1}$) per residue taking into account the peptide concentration determined by amino acid analysis.

Fluorescence Anisotropy Binding Assays

Measurements were performed on a Tecan infinite F500 equipped with polarizing filters and using excitation and emission wavelengths at 485 nm and 535 nm, respectively. Anisotropy data were calculated using the Magellan software version 6.5. Prior experiments, the mouse CC2-LZ was extensively dialyzed in binding buffer containing 20 mM HEPES pH 7.4, 100 mM NaCl, and 0.05% P20 detergent (v/v). All experiments were performed in a 384 well plate (vol 25 µl) at room temperature. The BODIPY®-labeled peptide concentrations were fixed at 0.1 or 10 µM whereas the CC2-LZ concentration varied from 0 to 100 µM. Reference calibrated at 22 mP, was based on the fluorescence of the peptide alone. Each experimental binding curve was determined from at least 10 independent concentration points. The G-factor was calculated as previously described in Agou et al. [7], with a value of 0.75, which was observed constant within 5% upon all titrations. For analysis, the blank value corresponding to the value of buffer alone, was subtracted from all titration data. The integration time was 20 Experiments were done in duplicate, and the $K_D$ was estimated by fitting the anisotropy data with the rectangular hyperbolic binding equation, using KaleidaGraph software as described elsewhere [1].

NF-κB inhibition Assays

NF-κB inhibition assay was almost similar to those previously described in [1], except that luminescence data were monitored with a Centro $XS^3$, LB960 luminometer (Berthold technologies.), which is more sensitive. All experiments were performed in duplicates in 96-well plates. Pre-B lymphocytes 70Z/3 C3 ($1.2 \times 10^5$) in 120 µl of RPMI 1640 medium, were incubated with a range from 0 to 10 µM of peptides, the control well being left untreated. After 2 h at 37° C., 5% $CO_2$, cell samples were divided in two parts: one was stimulated with 15 µg/ml of LPS from *Salmonella abortus equi* (Sigma, L 5886), the other was left untreated. After 4 h incubation, cells were centrifuged 7 min at 400×g, at 4° C. The cell pellets were washed once with cold PBS, lysed in 100 µl of 25 mM Tris-phosphate buffer pH 7.8, 1 mM DTT, 1% Triton X-100, 15% glycerol, 8 mM $MgCl_2$ (lysis buffer) and protease inhibitor (Roche) and then centrifuged at 1000×g for 20 minutes at 4° C. 50 µl of the supernatants were mixed with 4 µl of reaction substrate (which contains Galacton star™) and 196 µl of reaction buffer (luminescent beta-galactosidase detection kit II, Clontech).

For assessing intracellular stability of stapled peptides, cells were incubated 2 h, 37° C., 5% $CO_2$, followed by one wash in pre-warmed PBS (37° C.), and re-incubated with complete medium overnight. After 30 hours, cells were stimulated with LPS, and inhibition activity of peptides on the NF-κB pathway was completed as described above.

Cellular Uptake of NEMO Stapled Peptides

The cell penetration properties of NEMO stapled peptides were both determined by fluorescence microscopy and FACS.

Fluorescence Microscopy $2.2 \times 10^5$ cells for 220 µl/wells of 70Z3-C3 were incubated with 10 µM of BODIPY®-labeled peptide for 2 h at 37° C., 5% $CO_2$. Cells alone or incubated with BODIPY®-labeled BSA (ref) or BODIPY®-UBI devoid of the antennapedia cell penetrating sequence gave similar fluorescent background and were used as negative internal control, whereas cells with BA-UBI [1] at 10 µM were used as positive control. Cells were then plated on poly-L-lysine-coated glass coverslips and centrifuged at 300×g for one minute at room temperature. Cells were washed twice with cold PBS in order to remove any excess peptide. Fluorescence microscopy was performed after cell fixation either with 4% PFA (w/v) fixation or 100% Methanol. For methanol fixation, cells were first dehydrated on ice with 100% methanol for 5 minutes and progressively re-hydrated with ethanol (95%, 85%, 50%), for 1 min each. For PFA fixation, cells were fixed with 4% PFA for 20 minutes, at room temperature. Following fixation, samples were washed three times in PBS and incubated with DAPI used at 1:20 000 (Sigma-Aldrich, final concentration 62.5 ng/ml). After three additional washes, glass coverslips were mounted in mowiol (Mowiol® 4-88, glycerol, TrisBiovalley) followed by analysis on a Zeiss Imager Z1 microscope, at 63× objective oil lens. Images were acquired with AxioVision software and analysed later on with ImageJ version 2.0.0-rc-15 freely available at www.fiji.sc. For some experiments, confocal microscopy was also used to optimize picture's sharpness, and so was qualitatively more accurate to determine intracellular distribution of the peptide into the cell.

FACS Analysis $2.2 \times 10^5$ cells in 100 µl of 70Z3-C3 were incubated with either 10 µM or with various doses of 10 µM, 5 µM and 1 µM of labeled-peptides at 37° C., 5% $CO_2$. Similarly to fluorescence microscopy experiments, cells alone or incubated with BODIPY®-labeled BSA (ref) or BODIPY®-UBI devoid of the antennapedia cell penetrating sequence were used as negative control, whereas cells with BA-UBI [1] at 10 µM were used as positive control. After 2 h incubation, cells were washed 4 times with PBS at room temperature, and finally diluted 1:3 in PBS before subjected to FACS analysis. Along with the BODIPY® fluorophore the fluorescence intensity was recorded at 525±25 nm using the Gallios Flow cytometer (Beckman Coulter) to analyse each cells sample. Each internalization peptide was assessed by gating a population of 15,000 events and the data were analysed using Kaluza software version 1.2.

Cell Viability Assay Based on Resazurin Reduction Assay

The CellTiter-Blue® Cell Viability kit assay purchased from Promega was used to assess the cell death induced by NEMO stapled peptides in ABC- and GCB-DLBCL cell lines. Cells were incubated at a density of 250,000 cells/well in the presence of various concentrations of NEMO stapled peptides (0 to 10 µM), MALT1 peptide inhibitor (25 to 125 µM, Z-VRPR-fmk, Enzo Life Sciences), or IKKβ inhibitors (0.5 to 100 µM MLN120B, Medchem Express or PHA408, Axon Medchem). Cells were considered 100% death when the fluorescence intensity value was the same as the one with the medium alone or with the cells treated with the cycloheximide protein synthesis inhibitor at 25 µM (Sigma Aldrich).

The i,i+7 UBI-SAHN I307-A314 peptide which does not inhibit the NF-kB pathway and which does not bind at all NEMO was-used-as negative control. For each time point measurement 100 µl of cell samples were withdrawn at different incubation times (7 h, 24 h and 48 h) and subjected to resazurin assay for one hour at 37° C. in the $CO_2$ incubator by adding and mixing for 10 sec 20 µl of resazurin. Fluorescence measurements were performed with a TECAN infinite F500 instrument at 560 nm excitation wavelength and 590 nm emission wavelength. Viability of cells at time 0 was determined just before adding compound and all experiments were performed in duplicate.

The percentage of cell death was calculated according to the following formula: $(1-((RFU_{obs}-blank)/(RFU_{100\% \ viability}-blank))*100)$, where $RFU_{obs}$ corresponds to the cells viability observed in the presence of compound, $RFU_{100\% \ viability}$, the initial cells viability and blank the background fluorescence measured using the medium alone.

The $EC_{50}$ value was calculated by plotting the percentage of cell death as function of the compound concentration and fitting the experimental curve with the following formula: $(A*P_0)/(EC_{50}+P_0)$, where A is the amplitude of fluorescence, $P_0$ is the peptide concentration.

Cellular Uptake of the Stapled Peptide BA-UBI SAHN$_{D306-Q313}$

For determination of cellular uptake by flow cytometry, the BA-UBI-SAHN$_{D306-Q313}$ stapled peptide was first incubated with $2.2 \times 10^5$ 70Z3-C3 cells in 220 either at 4° C. or 37° C. for 2 h. Bodipy-labeled BSA, bodipy alone and bodipy-UBI were used as negative controls to verify the washing quality and efficient removal of any non-specific binding at the cell surface before FACS analysis. For experiments with endocytosis inhibitors, cells were first pre-treated for 30 min with either chlorpromazine (100 µg/ml, Sigma Aldrich), nystatin (50 µg/ml, Sigma Aldrich), or EIPA (5-(N-Ethyl-N-isopropyl) amiloride, (100 µM, Sigma Aldrich) before incubating with 10 µM of NEMO stapled inhibitor. After 2 h of incubation, cells were washed four times with PBS at room temperature and diluted at 1:3 in PBS for FACS analysis. Samples were analyzed as previously described in the European patent (No: 15307137.8).

Efficiency of Cell Death Induction and Cell Death Induced-Mechanism of NEMO Stapled Inhibitor To compare the inhibition efficiency of BA-UBI-SAHN$_{D306-Q313}$ with IKK inhibitors (MLN120B, MedChem Express) or IKKα/β inhibitor (TPCA1, R&D systems), 25,000 DLBCL cells (OCI-Ly3) were incubated for 7 h with an increasing concentration of IKK inhibitors ranging from 0 to 50 µM, and the amount of cell death was then determined using CellTiter-Blue® Cell Viability kit assay. For the MI-2 MALT1 inhibitor (Fontan et al., 2012, Cancer cell 22, 812-824), similar experiments were carried out in MALT dependent (OCI-Ly3) and independent (HLY1) DLBCL cells using a 0-25 µM range.

For experiments dedicated to cell death induced-mechanism, 25,000 DLBCL cells were first pre-treated with different apoptosis and necroptosis inhibitors before incubating at 10 JIM for 7 h with the NEMO stapled inhibitor (A-UBI-SAHN$_{D306-Q313}$) Z-VAD-fmk, a pan caspase inhibitor (Merck Millipore), was used with a range of 1 to 100 µM; Necrostatin-1 (Neel), a RIPK1 inhibitor (Tocris Bioscience), a range of 10-100 µM; Gsk872, a RIPK3 inhibitor (Merck Millipore), a range of 0.5-50 µM); Necrosulfonamide (NSA), a MLKL inhibitor (Merck Millipore), a range of 10-300 µM. Ferrostatin-1, an inhibitor of ferroptosis (Sigma Aldrich) was used at 25 µM, the mixture of pepstatin-A and E64D (Sigma Aldrich), inhibitors of lysosomal cathepin D and cathepsin B, respectively, at 25 µM each and Cyclosporin A (Sigma Aldrich), a CypD inhibitor, at 25 µM. In all experiments, the effect of different DMSO concentration on cell viability was measured and taken into account, and fluorescence background was measured using cell free medium containing inhibitors. The cell viability assay (CellTiterblue, Cell viability assay, Promega used) was previously described in the European patent (No: 15307137.8).

EXAMPLE 2: DESIGN AND SYNTHESIS OF STABILIZED α-HELICAL PEPTIDOMIMETICS MIMICKING THE NOA/UBAN UBIQUITIN BINDING SITE OF NEMO

Based on structural model of the human CC2-LZ complex with a MI or K63 diubiquitin chain (see Material and Methods), three i, i+4 and two i, i+7 stapled NEMO peptides as well as a peptide containing α-amino-isobutyric acid (Aib) residues (hereafter denoted UBI-Aib) were designed and synthesized. Aib residue—which differs from Ala residue by an additional methyl group on its Cα—often promotes α-helix structure by constraining φ-ψ angles in the helical region of conformational space [8]. The precise peptide sequence of NEMO α-helical peptidomimetics (Aib and staples) and their chemical syntheses are described in details under Materials and Methods is shown in Table III.

All these modified peptides were derived from the UBI peptide, which was previously shown to specifically inhibit the NF-κB activation [1]. As control, a mutant of i, i+7 stapled peptide (hereafter denoted Co-SAHN I307-A314), which is unable to bind to the NOA/UBAN/CC2-LZ domain of NEMO even at a high concentration was also generated. One version of UBI-Aib, i, i+4 stapled peptide and i, i+7 stapled peptide (Table III) with a 16-residue extension derived from the antennapedia/penetratin sequence was also generated to ensure their internalization into the cell. For clarity, the i+4 and i+7 stapled peptides are referred to as UBI-SAHN$_{X-Y}$ (Stapled A⎵⎵⎵⎵-Helical NEMO), the residue number written in subscript indicating the exact position of the hydrocarbon bridge within the peptide (human numbering), and the peptides with the antennapedia CPP sequence are referred to as A-UBI, A-UBI-Aib and A-UBI-SAHN$_{X-Y}$. Importantly for each synthesis of i+7 stapled peptides, two different peptide products with the same molecular mass were observed as judged by mass spectrometry analysis but with different elution profiles in HPLC. The RMN analysis of the i,i+7 stapled peptide UBI-SAHN$_{A303-A310}$ confirmed the presence of two different conformers: one conformer bearing the hydrocarbon bridge in cis conformation (arbitrarily denoted A), the other conformer bearing the hydrocarbon bridge in trans conformation (B). Thus, syntheses of two i,i+7 stapled peptides resulted in four different conformers, which were all analyzed individually.

EXAMPLE 3: ANALYSIS OF NEMO STAPLED AND AIB PEPTIDES BY CD SPECTROSCOPY

To assess α-helical-induced structuration by the insertion of Aib residues, i,i+4 or i,i+7 staples, all NEMO peptides were analyzed by CD spectroscopy. As internal control, the parental UBI was also analyzed in the helix-stabilizing solvent trifluoroethanol (TFE) and at 1° C. to evaluate the maximal helicity of the peptide. As shown in FIG. 1, UBI adopts a fully α-helical monomeric structure under these experimental conditions and was taken as the reference spectrum for a 100% α-helical conformation in all experiments. Remarkably, all of the stapled and Aib peptides showed double negative dichroic bands at 208 and 222 nm and a positive dichroic band at 192 nm, characteristic of α-helical structure (FIGS. 1A, B and C). In contrast, the UBI parental peptide showed a broader negative band at 205 nm corresponding only to 42% helicity and thus predominantly exists as a random coil. All of the stapled peptides exhibited a significant increase in α-helicity compared with the Aib peptide, indicating more helical stabilization of i,i+4 and i,i+7 stapling. Furthermore, the i,i+7 stapled peptides (UBI-SAHN$_{D306-Q313}$ (A and B), UBI-SAHN$_{A310-A310}$ (B)), except for the UBI-SAHN$_{A310-A310}$ conformer A (63%), exhibited additive enhancement in α-helical content (75-80%) compared with all i+4 stapled peptides ranging from 57 to 70%, which suggests that i,i+7 stapling in this context optimally reinforces the α-helical structure of UBI. Notably, it was observed that the cis or trans conformation of the i,i+7 hydrocarbon link can modulate the helicity of the peptide. Indeed, the conformer B of UBI-SAHN$_{A303-A310}$ displays 80% helicity, whereas the other conformer A displays only 63%. This conformer-dependent helicity depends on the insertion of the i,i+7 staple in the peptide since no difference in helicity was observed between the two conformers of the other i, i+7 stapled peptide UBI-SAHN$_{D306-Q313}$.

Thermal stability of the peptides was also investigated by performing thermal denaturation profiles followed by CD (FIGS. 1 C and D and Table III). Consistent with the role of Aib residues in a peptide sequence, insertion of Aib residues in UBI resulted in a more pronounced effect on helix stabilization rather than helix formation. Indeed, the helicity of UBI-Aib (49%) is only 1.16-fold increased at 1° C. compared to UBI (42%), while its melting temperature (Tm=-8° C.) is 2.25 times higher than that of UBI (Tm=-18° C.). Overall, the i, i+7 stapled UBI peptides (Tm 32-35° C.) were significantly more stable than its counterparts i,i+4 (Tm 15-20° C.) and about 40° C. and 50° C. more stable than UBI-Aib (Tm=-8° C.) and UBI (Tm -18° C.).

EXAMPLE 4: DETERMINATION OF BINDING AFFINITIES BY FLUORESCENCE POLARIZATION FOR THE NOA/UBAN/CC2-LZ DOMAIN OF NEMO

All NEMO peptides were conjugated to an extra N-terminal cysteine with the fluorophore BODIPY® or FITC to determine their binding affinity for the CC2-LZ domain of NEMO (also called NOA or UBAN) by fluorescence polarization. For each peptide titration, various concentration of the target ranging from 0 to 100 μM and a fixed concentration of peptide at 0.1 or 10 μM were used at 25° C. For all peptides, different binding constants ($K_D$s) were observed when titration experiments were carried out at 0.1 or 10 μM peptide concentration, binding affinities being always weaker at a peptide concentration of 10 μM than 0.1 μM. Titration experiments between labeled and unlabeled peptides revealed that this concentration-dependent effect was not only due to self-association properties of peptides at 10 μM but rather to dimerization properties of the CC2-LZ target which weakly dimerizes with a $K_D$ of 48 μM at 10° C. [10]. For these reasons, all further titration experiments were performed with a fixed peptide concentration of 0.1 μM unless otherwise indicated.

No binding activity was observed with the UBI peptide (21 aa) devoid of the antennapedia/penetratin N-terminal sequence. In contrast, a $K_D$ value of 4±1 μM was measured with A-UBI (37 aa), which is consistent with previously reported binding data using a fixed peptide concentration of 10 μM ($K_D$=17 μM, [1]). The contribution of the antennapedia in the binding was due to the addition of an extra N-terminal sequence (16 aa) irrespective of the nature of the sequence. Indeed, similar contributions in the binding were also observed with other CPPs (TAT: $K_D$=24±4 μM; R9: $K_D$=12±3 μM; R7: $K_D$=12±3 μM) which totally differ in their peptide composition. One possible explanation could be that increasing the N-terminal length of peptide may preserve crucial contacts between the first residues of UBI and the target, which could not occur with UBI alone due to end-fraying.

Although UBI-Aib was more stable than UBI, there was no gain in affinity without or with N-terminal antennapedia sequence, and a similar $K_D$ of 5 μM 2 μM was obtained with A-UBI-Aib (Table IV).

In contrast, all antennapedia-free i,i+4 and i,i+7 stapled peptides exhibit significant increased binding affinity compared to UBI ranging from 34 to 360 μM (FIG. 2 and Table IV). The most potent CPP-free stapled peptide was the conformer A of the UBI-SAHN$_{D306-Q313}$ i+7 stapled peptide with a $K_D$ of 34±6 μM. Overall, it was found that the enhanced α-helicity and stability of stapled peptides strongly correlate with the improvement of binding affinity, validating the stapling technology as a powerful tool for improving NEMO peptide candidates.

Importantly, like A-UBI and A-UBI-Aib, addition of the antennapedia sequence to stapled peptides considerably increased binding affinity with $K_D$s values in the medium nanomolar range. The i,i+7 stapled peptides were the most potent binders. Indeed A-UBI-SAHN$_{A303-A310}$ (conformer B) exhibited the highest binding affinity (20 nM), followed by A-UBI-SAHN$_{D306-Q313}$ (A, 60 nM and B, 50 nM) and the i,i+4 staple A-UBI-SAHN$_{A310-A314}$ (200 nM)

Altogether, the combination of the i,i+7 stapling technology with the addition of antennapedia (16 aa) allowed to isolate high affinity binders to NEMO, with 80-200 fold enhancement in NEMO affinity compared to the parental A-UBI.

EXAMPLE 5: INHIBITORY ACTIVITY OF THE NF-κB PATHWAY BY NEMO PEPTIDES

Inhibition of NF-↓B activation following LPS stimulation was performed on NF-κB reporter pre-B 70Z3-C3 cells as previously described [1]. Experiments were first carried out with our A-UBI reference peptide containing the antennapedia sequence and compared to A-UBI-Aib, A-UBI-SAHN$_{A310-A314}$ (staple i+4) and A-UBI-SAHN$_{D306-Q313}$ and A-UBI-SAHN$_{A303-A310}$ (staple i+7). As shown in Table V and FIG. 3, all i+4 and i+7 stapled peptides bearing the antennapedia sequence displayed the best inhibitory activity with IC$_{50}$ values in a high nanomolar range (0.4-0.6 μM), corresponding to a 7-10 fold decrease relative to the A-UBI parental peptide (IC$_{50}$: 4±1 μM).

Contrary to in vitro data, no change in inhibition activity was observed between conformers A and B of i+7 stapled peptides. The Aib peptide exhibited only a 2.7-fold improvement in inhibition potential (IC$_{50}$: 1.5±0.5 μM), again demonstrating that NEMO stapling was more powerful than the insertion of Aib residues. Unexpectedly, no inhibition activity was observed with all Aib and stapled peptides devoid of the antennapedia sequence. These results were surprising since in vitro binding affinity for NEMO target of some stapled peptides such as UBI-SAHN$_{D306-Q313}$ (A) were in the same concentration range than that of parental UBI.

EXAMPLE 6: CELL PENETRATION OF STAPLED PEPTIDES WITH AND WITHOUT ANTENNAPEDIA (CPP)

The absence of NF-κB inhibition with all of the antennapedia-free stapled NEMO peptides could reflect a defect in cellular internalization, although it is generally believed that mono-stapled peptides are intrinsically cell permeable [12]. To determine whether NEMO stapled-peptides without antennapedia exhibited a defect in cellular internalization, their uptake was analysed in 70Z3-C3 cells using Gallios FACS. As shown in FIG. 4, the A-UBI positive control showed two peaks: the first peak had a median at 36 corresponding to cells with a small amount of internalized peptides and the second one had a median at 144 referring to cells with important internalization of peptide. The peptide reference antennapedia-free UBI, which exhibits no inhibition activity gave a peak medium at 20 indicating a defect in cellular uptake and so was taken as negative control. Of note, the autofluorescence of untreated cells were similar to those incubated with BODIPY® alone or BODIPY®-BSA, indicating that the BODIPY® alone or conjugated with BSA is not intrinsically cell permeable under our conditions. As expected, all inhibitory stapled peptides with antennapedia sequence showed very good internalization, which was similar to the A-UBI positive reference (FIG. 4).

Next all of the stapled peptides devoid of CPP sequence were compared. UBI-SAHN$_{A303-B307}$ peptide (i, i+4) gave only one peak with a median at 10. UBI-SAHN$_{D306-A310}$ peptide (i, i+4) gave two peaks: one at 1, and the other one at 35, reflecting a weak internalization relative to UBI negative control (FIG. 4A.) Similar experiments were obtained with two of i,i+7 stapled peptide, and it was observed that UBI-SAHN$_{A303-A310}$ displayed only one peak with the median at 8, while UBI-SAHN$_{D306-Q313}$, like UBI-SAHN$_{D306-A310}$, showed two peaks with one at 8 and the other at 52 reflecting again a weak internalization of peptide compared to negative control (FIG. 6 B). All these data were further confirmed using fluorescence microscopy (not shown).

Therefore, these results clearly indicated that the absence of NF-κB inhibition by free-antennapedia stapled peptides was due to their defect in cellular internalization. Moreover, the i,i+4 and i+i+7 stapled peptides, UBI-SAHN$_{D306-Q313}$ and UBI-SAHN$_{D306-A310}$, showed a better internalization than the other stapled peptides, suggesting that the removal of negative charge of D306 residue increases cellular uptake of NEMO stapled peptides.

EXAMPLE 7: SYNTHESIS AND ANALYSIS OF MODIFIED STAPLED PEPTIDES DEVOID OF CPP SEQUENCE

In addition to the D306 residue, UBI-derived stapled peptides contain two glutamic acids residues (E) at position 315 and 320 (human numbering), which could also diminish the cellular uptake of antennapedia-free stapled peptides. Furthermore alanine scanning of A-UBI showed that mutagenesis of Glu315 and Glu320 did not disrupt the NEMO CC2-LZ interaction. Therefore Glu315 and Glu320 were replaced with either Glu-OMe or Gln residues in UBI-SAHN$_{D306-Q313}$ to create the stapled peptide sequences devoid of negative charges termed UBI-SAHN$_{D306-Q313}$ OMe and UBI-SAHN$_{D306-Q313}$ Q/Q. These modified i,i+7 stapled peptides were then evaluated for their ability to in vitro bind to NEMO target, internalize into the cell and inhibit specifically the NF-κB pathway (FIG. 5). Consistent with the alanine scan, UBI-SAHN$_{D306-Q313}$ OMe and UBI-SAHN$_{D306-Q313}$ Q/Q exhibited similar binding affinities as the WT with $K_D$s of 24±5 and 23±3 μM, respectively. Moreover, addition of the antennapedia sequence in UBI-SAHN$_{D306-Q313}$ OMe, like the WT, significantly improved the binding constant with a $K_D$ of 60±10 nM which was equivalent to the WT (FIG. 5).

More importantly, and contrary to the WT UBI-SAHN$_{D306-Q313}$, both UBI-SAHN$_{D306-Q313}$ OMe and UBI-SAHN$_{D306-Q313}$ Q/Q became cell permeable as judged by FACS experiments (FIG. 6). This indicated that the combination of the hydrocarbon staple with the removal of three native negative charges (Asp406, Glu315 and Glu320) in UBI-derived stapled peptides was absolutely necessary to make stapled peptides fully permeable to the cell. Consistently with the enhanced cell permeability, both modified stapled peptides became very good NF-κB inhibitors with IC$_{50}$ values of 1.9±0.03 μM for UBI-SAHN$_{D306-Q313}$ OMe and 0.8±0.03 μM for UBI-SAHN$_{D306-Q313}$ Q/Q, which was close to the IC$_{50}$ value of the best NEMO stapled peptide inhibitor containing the antennapedia sequence (0.43 μM). A similar double substitution Glu-Gln was also carried out in the i, i+4 stapled UBI-SAHN$_{D306-A310}$. However, its inhibitory activity was slightly weaker than i, i+7 UBI-SAHN$_{D306-Q313}$ Q/Q with an IC$_{50}$ value of 1.3±0.2 µM.

Taken together, these data clearly indicated that the absence of inhibitory activity for all of antennapedia-free stapled peptides was due to a defect in cell internalization and that modifications of some stapled peptides such as UBI-SAHN$_{D306-Q313}$ Q/Q allowed to isolate NEMO stapled peptides with NF-kB inhibition potential similar to stapled peptides containing the antennapedia sequence. This could be of great importance for further pharmacological studies since previous data showed that CPP positively charged like antennapedia can exhibit in vivo poor serum stability and considerable cytotoxicity[13].

EXAMPLE 8: SPECIFIC INDUCTION OF CELL DEATH IN DLBCL CELL LINES BY NEMO STAPLED PEPTIDE

To validate the NF-κB inhibition potential of NEMO stapled peptides in tumoral cells, the effect of the i,i+7 stapled peptide A-UBI-SAHN$_{D306-Q313}$ on the viability of human activated B-cell (ABC) diffuse large B-cell lymphoma (DLBCL) cells was next tested. These ABC DLBCL lymphomas, which are the most aggressive lymphomas (30-40% of all lymphomas) characterized by NF-κB hyperactivation, have an inferior prognosis relative to those with the center B-cell (GCB subtype), which do not exhibit elevated NE-03 activation. GCB-DLBCL cell lines such as OCI-Ly7 were then used to evaluate the selectivity of NF-κB inhibition of A-UBI-SAHN$_{D306-Q313}$. Moreover, numerous studies previously reported that the oncogenic potential of ABC-DLBCL was associated with constitutive activation of the NF-κB pathway, which results from chronic activation of BCR pathway (also called MALT dependent) or/and TLR (MALT independent) pathways. Of note, most anti-cancer drugs that are under development in the pharmaceutical industry target the BCR pathway but not the TCR pathway. It is therefore expected a lack of effectiveness of these products on ABC-DLBCLs in which the activation of the NF-κB pathway results from the oncogenic activation of TLRs pathways such as MYD88 (MALT independent). To this end, the novel stapled-peptide inhibitor of NEMO, A-UBI-SAHN$_{D306-Q313}$, was tested on human cell lines derived from ABC-DLBCL subtype in which chronic activation of NF-κB results either from the oncogenic activation of the BCR pathway (OCI-Ly3) or from of the TLR pathway (HLY1; Jackson et al. [15]; Fontan et al. [16], Nagel et al. [17]).

The induction of necroptotic/apoptotic cell death induced (or not) by the NEMO stapled peptide in these different DLBCL human cell lines was evaluated using cell viability assay based on resazurin reduction assay as described in material and methods.

As shown in FIG. 7, it was observed that A-UBI-SAHN$_{D306-Q313}$ induced 100% of cell death on OCY-Ly3 ABC-DLBCL cells (MALT1-dependent) after short incubation time of 7 h, with no further change at 24 h and 48 h, underlining a fast activation of induced cell death. UBI-SAHN$_{I307-A314}$, which does not interact in vitro with NEMO CC2-LZ target and does not inhibit LPS-induced NF-kB activation (Table V), despite its enhanced helicity and thermal stability induced by the i,i+7 staple (Tables III and IV), showed no effect of cell death even at 48 h. For this reason, this NEMO stapled peptide termed Co-UBI-SAHN$_{I307-A314}$ was taken as negative control in all further experiments. The induction of cell death on OCY-Ly3 cells was also compared with a specific inhibitor of IKKβ kinase called MLN120B and a peptide inhibitor of the paracaspase MALT1 called Z-VRPR-FMK. MLN120B displayed 38% of cell death at 7h and reached 52% at 48 h, while Z-VRPR-fmk (Z-Val-Arg-Pro-Arg-fluoromethylketone) only showed very little cell death after 48 h, not comparable at all with other inhibitors tested. EC$_{50}$ values of A-UBI-SAHN$_{D306-Q313}$ slightly differ with incubation time ranging from 2.6±5 µM at 7 H, 2.1±0.1 µM at 24 H to 5±0.1 µM at 48 H (FIG. 7). On the other hand, EC$_{50}$ of MLN120B calculated on the basis of 52% of cell death at 48 h was 125±10 µM, indicating that A-UBI-SAHN$_{D306-Q313}$ is about 50 times more potent than ML120B IKKβ inhibitor.

Similar experiments were performed on HLY1 ABC-DLBCL cell lines, which constitutively activate the IKK/NF-kB pathway in a MALT1 independent manner through the chronic activation of TLR pathway. As expected, treatment of cells with the Z-VRPR-fmk MALT1 inhibitor did not induce any cell death for at least 48 h (FIG. 8). By contrast, A-UBI-SAHN$_{D306-Q313}$ strongly induces a cell death, with 100% of cell death observed at 7 h and EC$_{50}$ values ranging from 0.65 to 1.1 µM depending on incubation time. No cell death was observed at 7 h with IKKβ inhibitor, but similar EC$_{50}$ could be determined at 24 h and 48 h equivalent to 70±2 µM and 78±2 µM, respectively, indicating again that A-UBI-SAHN$_{D306-Q313}$ is more potent than ML120B (70x). The effect of the NEMO stapled peptide on the induction of cell death was very specific in OCY-Ly3 and HLY1 cells since no cell death was observed in OCY-Ly7 (GCB-DLBCL), which does not display any constitutive NF-κB activation (Jackson et al. [15]; Fontan et al. [16], Nagel et al. [17]; FIG. 9). Similar effect was also observed with ML120B and Z-VRPR-fink inhibitors. Of note, a similar result was also obtained on other cell lines derived from ABC-DLBCL (U2932), which did not show any chronic NFκB activation as judged by the P65 nuclear translocation assay using fluorescence microscopy (not shown).

Altogether, these data provide a conceptual proof for a clinical application of NEMO stapled peptides in the treatment of ABC-DLBCL and in other types of cancer linked to chronic NF-κB activation.

EXAMPLE 9: CHARACTERIZATION OF CELL DEATH INDUCED BY NEMO STAPLED PEPTIDES: APOPTOSIS OR NECROPTOSIS?

The characterization of cell death induced by NEMO stapled peptides could be of great pharmaceutical interest if one considers that regulated necrosis (also called necroptosis) is more inflammatory than apoptosis. In general, necroptosis is believed to be a more potent inducer of inflammation than apoptosis (although this concept should be further validated in vivo experimental models). This is mainly due to the fact that damage-associated molecular patterns (DAMPs) like cytokines and alarmins, which act as danger signals to alert the immune system, are primarily released by cells undergoing necrosis. As a consequence, one could predict that if NEMO inhibitors induce more regulated necrosis than apoptosis in tumoral cells, it could accentuate the release of cytokines and chemokines in the tumor microenvironment, facilitate the recruitment of T cells, and so may have a potential interest in anti-cancer immunotherapy.

To better characterize cell death induced by NEMO stapled inhibitors, OCY-Ly3 cells were incubated with A-UBI-SAHN$_{D306-Q313}$ and necrostatin-1 (Nec-1), which is a specific inhibitor of RIP/RIPK1 kinase activity. In parallel, similar experiments was carried out with the pan-caspase inhibitor Z-VAD-fmk. Remarkably, it was observed that Nec1, but not Z-VAD-fmk, totally prevent the induction of cell death by A-UBI-SAHN$_{D306\text{-}Q313}$. This strongly suggests that pharmacological inhibition of NEMO by stapled peptides preferentially induces regulated necrosis in OCY-Ly3 tumoral cells. These data are also consistent with genetic deletion of NEMO, which recently showed that NEMO acts in a NF-κB independent manner as negative regulator of regulated necrosis in TNF signaling [14].

EXAMPLE 10: MECHANISMS OF CELLULAR UPTAKE BY THE MOST POTENT STAPLED NEMO INHIBITOR, A-UBI-SAHN$_{D306\text{-}Q313}$ Despite the modification of the natural UBI inhibitor using stapling technology, it has been showed above that some stapled versions of UBI do not efficiently penetrate into the cell. Accordingly, no inhibition of the NF-κB pathway was observed with these stapled versions of UBI. Moreover, previous studies showed that the CPP antennapedia alone or associated with a protein or an oligonucleotide cargo use both passive diffusion and active transport to internalize into the cell (Dupont, Prochiantz & Joliot, Methods Mol. Biol. vol 663, DOI 10.1 etc.). Conservely, internalization of stapled peptides was shown to occur only via active transport and through a clathrin- and calveolin-independent endocytosis pathway (Verdine et al., 2015 med chem, 6 111-119). Therefore, the inventors next investigated the uptake mechanism of A-UBI-SAHN$_{D306\text{-}Q313}$. This stapled peptide was found to be the most potent stapled NEMO inhibitor and it is made up of a combination of the antennapedia sequence with a hydrocarbon i+7 staple, raising the question whether its internalization occurs through a passive or active transport. As shown in FIG. 10A, the intracellular delivery of the peptide analyzed by flow cytometry upon incubation of 70Z3-C3 pre-B lymphocytes for 2 h at 4° C. was 58% lower than that at 37° C. (control), indicating that A-UBI-SAHN$_{D306\text{-}Q313}$ was internalized into cells via an energy-dependent endocytosis mechanism.

To further decipher the endocytosis mechanism, the inventors then employed several well-established endocytosis inhibitors such as chlorpromazine (CPZ), an inhibitor of clathrin-dependent endocytosis, nystatin (NYS), an inhibitor of calveolin-mediated endocytosis and ethylisopropylamiloride (EIPA), an inhibitor of macropinocytosis (FIG. 10B). Cells were pre-incubated in a dose-dependent manner with these different endocytosis inhibitors for 30 min before treatment with A-UBI-SAHN$_{D306\text{-}Q313}$ and the cellular uptake was determined by flow cytometry. Treatment with nystatin (50 μg/ml), chlorpromazine (10 μg/ml) and ethylisopropylamiloride (100 μM) significantly reduced the uptake of the stapled peptide by 50%, 59% and 26%, respectively. Altogether, these results indicate that the A-UBI-SAHN$_{D306\text{-}Q313}$ stapled NEMO peptide, which combines the CPP antennapedia with the i+7 hydrocarbon does not follow a single endocytosis mechanism for its cellular uptake, but rather a complex combination of various processes such as clathrin-mediated, calveolae-mediated endocytosis mechanisms and macropinocytosis.

EXAMPLE 11: NEMO STAPLED INHIBITOR TRIGGERS CELL DEATH INDUCTION IN ABC-DLBCL THROUGH A SPECIFIC RIPK1/RIPK3/MLKL-MEDIATED NECROPTOSIS PATHWAY

In TNF signaling pathway, it has been shown that two sequential cell death checkpoints that protect TNF-mediated cell death can be initiated: a late NF-κB-dependent cell death checkpoint and an early NF-κB transcription factors-independent cell death checkpoint (see Ting & Bertrand for a review). The late checkpoint has been described for many years (Karin review) and occurs upon induction of pro-survival genes by NF-κB transcription factors, such as cIAP1/2 and c-FLIP. Disrupting this late checkpoint by inhibiting NF-κB leads to apoptosis induction in a receptor interacting protein kinase 1 (RIPK1)-independent manner in response to TNF receptor 1 (TNFR1) ligation. The early cell death checkpoint, on the contrary, was discovered more recently in TNF signaling and is NF-κB transcription-independent ((A. Ting, Vanderbelleme, Manolis and Ursini etc. . . . ). Several lines of evidences showed that it is initiated by RIPK1 ubiquitylation, which leads to NEMO recruitment and IKK activation. NEMO protects the ubiquitination status of RIPK1 and keeps RIPK1 in survival mode, preventing it from activating downstream death-signaling molecules. Disruption of this checkpoint via genetic or pharmacological inhibition can induce apoptosis or necroptosis upon TNFR1 ligation.

Nowadays, too little is known about this early cell death checkpoint in both BCR and TLR pathways, which ultimately leads to chronic and permanent activation of NF-κB in ABC-DLBCL. In particular, it is unclear whether the RIPK1/RIPK3 necrotoptic complex (also called necrosome) systematically originates from the apoptotic complex composed of RIPK1-FADD-Caspase 8 or whether it forms in parallel. Indeed, the RIPK1/RIPK3 necrosome has been reported to form independently of FADD and Caspase 8. Modulating this checkpoint could be of great interest in anticancer therapeutic strategy, especially under circumstances where oncogenic pathways and tumors co-opt this checkpoint to enhance survival during transformation. As example of the first described pharmacological disruptors of the early checkpoint, one can mention SMAC mimetics, which disrupt the early checkpoint in TNF signaling by causing the degradation of cIAP1/2. In the case of NEMO inhibitor, the simple analysis of cell death morphology under microscope showed clearly typical features of necrotic cells (oncosis, plasma membrane rupture, swelling of organelles) rather than those of apoptotic cells (pyknosis, nuclear fragmentation, plasma membrane bledding, rounding-up of the cell).

In order to investigate in details the form of cell death induced by A-UBI-SAHN$_{D306\text{-}Q313}$, hereafter denoted NEMO stapled inhibitor, the inventors first employed several well-established inhibitors involved in the predominant form of regulated necrotic cell death called RIPK1/RIPK3/MLKL pathway. To this end, ABC-DLBCL cell lines (OCY-Ly3) were first pre-treated with an inhibitor of RIPK1, necrostatin-1 (Nec1), before adding the NEMO stapled inhibitor. The cell viability of DLBCL was then determined after 7 h, 24 h and 48 h incubation as described in Material and Methods. As shown in FIG. 11A, the pre-treatment of OCY-Ly3 cells provided almost complete protection to cell death induced by NEMO stapled inhibitor (85% of cells became resistant to NEMO inhibitor). This protection effect was dose-dependent and suggested that cell death occurs through RIPK1-dependent regulated necrosis pathway. Similar experiments were performed with GSK872, an inhibitor of RIPK3, and necrosulfonamide (NSA), and inhibitor of mixed lineage kinase domain-like (MLKL). Again, we observed that GSK872 and NSA inhibitors significantly rescued, albeit in a lesser extent, the cell viability of DLBCL cells. Of note, the extent of rescue correlated with the increasing concentration of GSK872 and NSA.

Importantly, the inventors found that the Z-VAD-fmk pan-caspase inhibitor alone or in combination with Nec1 did not provide any protection to cell death induced by NEMO inhibitor after 7 h and 24 h incubation (FIGS. 11A & B), clearly indicating that NEMO inhibitor does not induce any form of caspase-dependent apoptosis DLBCL cell lines.

Other forms of regulated necrosis were previously described such as ferroptosis (Yang & Stockwell 2008, Chem. Biol. 15, 235-245), mitochondrial permeability transition pore (MPTP)-mediated necrosis (Javadov & Kuznetsov 2013, Front Physiol. 4, 76) and uncontrolled cathepsin-dependent necroptosis (Boya and Kroemer 2008, oncogene 27, 6434-6451; Mohammad et al., 2015, Semin Cancer Biol. 35 S78-S103). Thus, to assess whether NEMO stapled inhibitor triggers cell death via a specific RIPK1/RIPK3/MLKL necrotopsis pathway in ABC-DLBCL cell lines, the inventors next investigated the cell death inducing effect of NEMO stapled peptide in the presence of specific inhibitors which are specific to these other forms of regulated necroptosis. As shown in FIG. 12, neither Ferrostatin-1 (inhibitor of ferroptosis), nor cyclosporin A (inhibitor of MPTP-mediated necroptosis) nor the pepstatinA/E64D mixture was able to rescue cell viability of OCY-Ly3 cells in the presence of NEMO stapled inhibitor. Therefore, these data indicate that none of other forms of regulated necrosis was initiated in the cell death induced by NEMO stapled inhibitor. Taken together, these results indicate that NEMO stapled inhibitor disrupts an early cell death checkpoint in DLBCL cell lines, leading to no apoptotic cell death but rather necroptotic cell death involving RIPK1/RIPK3/MLKL pathway.

EXAMPLE 12: COMPARATIVE STUDIES OF THE NEMO-STAPLED INHIBITOR, A-UBI-SAHN$_{D306-Q313}$, WITH OTHER WELL-ESTABLISHED INHIBITORS OF IKKα/β AND MALT-1 IN ABC-DLBCL

It has been previously showed that MLN120B IKK inhibitor—which specifically inhibits IKKβ-only exhibits a modest effect on cell death induction in several subtypes of ABC-DLBCL such as OCY-Ly3 cells (FIG. 4A and FIGS. 7 and 8 in the European patent (No: 15307137.8)). This minor effect could be due to the presence of IKKα activity, which could functionally compensate IKKβ inhibition. To this end, a similar experiment was performed with TPCA-1, a pan-IKK inhibitor which has been reported to inhibit both IKKα and IKKβ (IC$_{50}$=400 nM and 17.9 nM for IKKα and IKKβ, respectively). The inventors found no significant additional effect on cell death induction in the presence of the TPCA-1 pan-IKK inhibitor. Therefore, the NEMO stapled inhibitor is more potent than IKKα/β kinase inhibitors to promote cell death in cancer DLBCL cells and this is likely due to the crucial involvement of NEMO in both early and late cell death checkpoints.

As previously reported in the European patent (No: 15307137.8), MALT1 is a unique paracaspase protein that transduces aberrant oncogenic signaling in some ABC-DLBCL subtypes in which chronic NF-κB activation is triggered through BCR activation (MALT dependent, OCY-Ly3) but not through TLR pathway (MALT independent, HLY1). Indeed, the MI-2 small molecule which is a potent inhibitor of MALT1 was reported to be selective for MALT1-dependent cell lines such as OCY-Ly3, whereas the ABC-DLBCL MALT1-independent cell lines (HLY-1) was resistant (Fontan et al., 2012 Cancer Cell). Consistent with these published data, the inventors observed that MI-2 killed MALT dependent OCY-Ly3 cells with an EC$_{50}$ value of 2.5±0.05 μM (FIG. 13B), which is similar to that obtained with NEMO stapled inhibitor (EC$_{50}$=2.6±0.5 μM, FIG. 7 in the European patent No 15307137.8). By contrast, MALT independent HLY1 cell lines were more resistant to MI-2 treatment (FIG. 13B) whereas a complete induction of cell death was observed with NEMO stapled inhibitor with a EC$_{50}$ value of 0.65±0.1 μM (see FIG. 8 in the European patent No 15307137.8).

Therefore, contrary to the MI-2 inhibitor of MALT1, the NEMO stapled inhibitor (A-UBI-SAHN$_{D306-Q313}$) was able to kill both MALT dependent and independent ABC-DLBCL subtypes, indicating that NEMO inhibitor is more potent than MI-2 since a larger panel of chemoresistant ABC subtype is sensitive to its treatment.

TABLE I

Purification procedures and mass spectrometry data of all NEMO i,i+4 hydrocarbon-stapled peptides used

| R8/S5 oleline incorporation | A310S$_5$-A314 S$_5$ | A303 S$_5$-I307 S$_5$ | D306 R$_8$-A310 S$_5$ |
|---|---|---|---|
| Additional modifications | N-ter Apd sequence | | E315Q E320Q |
| Crude solubility | TFA 0.08% | TFA 0.08% + CH3CN | TFA 0.08% | TFA0.08% |
| Free thiol peptide purification procedure | MPLC C18 TFA 15%-60 min->60% B | MPLC C18 TFA 15%-60 min->60% B | Kromasil C18 TFA 20%-20 min->35% MeCN | MPLC C18 TFA 15%-60 min->60% B |
| Nem coupling | 2eq Nem-mld/crude-SH Phosphate buffer 0.1M pH6 | 2eq Nem-mld/crude-SH Phosphate buffer 0.1M pH6 | 2eq Nem-mld/crude-SH Phosphate buffer 0.1M pH6 | 3eq Nem-mld/purified-SH Phosphate buffer 0.1M pH6 |
| Nem peptide purification | Kromasil C18 TFA 20%-20 min->40% MeCN | Kromasil C18 TFA 25%-20 min->35MeCN | Kromasil C18 TFA 20%-20 min->40% MeCN | Kromasil C18 TFA 20%-20 min->40% MeCN |
| Nem peptide analytical procedure | Symmetry C18 TFA 20%-20 min->40% MeCN | Symmetry C18 TFA 25%-20 min->35% MeCN | Symmetry C18 TFA 20%-20 min->30% MeCN | Aeris peptide C18 TFA 20%-20 min->40% MeCN |
| Nem peptide average mass | theor 2907,3967 exp 2906,7505 | theor 5136,1425 exp 5136,2358 | theor 2865,3161 exp 2865,0840 | theor 2861,4170 exp 2861,5222 |
| Bodipy coupling | 1,2eq Bpy-mld/purified-SH Phosphate buffer 0.1M pH6 | 1,1eq Bpy-mld/purified-SH Phosphate buffer 0.1M pH6 | 1,2eq Bpy-mld/purified-SH Phosphate buffer 0.1M pH6 | 2eq Bpy-mld/purified-SH Phosphate buffer 0.1M pH6 |

TABLE I-continued

Purification procedures and mass spectrometry data of all NEMO i,i+4 hydrocarbon-stapled peptides used

| R8/S5 oleline incorporation | A310S₅-A314 S₅ | A303 S₅-I307 S₅ | D306 R₈-A310 S₅ |
|---|---|---|---|
| Bodipy peptide purification | Kromasil C18 TFA 25%-20 min->45% MeCN | Kromasil C18 TFA 25%-20 min->35% MeCN | Kromasil C18 TFA 30%-20 min->40% MeCN | Kromasil C18 TFA 24%-20 min->44% MeCN |
| Bodipy peptide analytical procedure | Aeris peptide C18 TFA 25%-20 min->35% MeCN | Aeris peptide C18 TFA 28%-20 min->38% MeCN | Aeris peptide C18 TFA 25%-20 min->35% MeCN | Aeris peptide C18 TFA 23%-20 min->43% MeCN |
| Bodipy peptide average mass | theor 3196,4893 exp 3195,9446 | theor 5425,2351 exp 5425,8457 | theor 3154,4087 exp 3155,1355 | theor 3150,5101 exp 3150,0791 |

TABLE II

Purification procedures and mass spectrometry data of all NEMO i,i+7 hydrocarbon-stapled peptides use

| R8/S5 olefine incorporation | D306 R₈-Q313 S₅ | | | | |
|---|---|---|---|---|---|
| Additional modifications | | N-ter Apd sequence | E315MeGlu E320MeGlu | N-ter Apd sequence E315MeGlu E320MeGlu | E315Q E320Q |
| Crude solubility | TFA 0.08% | TFA 0.08% | TFA 0.08% | TFA 0.08% | TFA 0.08% |
| Free thiol peptide purification procedure | MPLC C18 TFA 20%-60 min->70% B | MPLC C18 TFA 15%-60 min->60% B | MPLC C18 TFA 20%-60 min->60% B | MPLC C18 TFA 20%-60 min->70% B | MPLC C18 TFA 20%-60 min->60% B |
| Nem coupling | 2,8eq Nem-mld/crude-SH Phosphate buffer 0.1M pH6 | 3eq Nem-mld/purified-SH Phosphate buffer 0.1M pH6 | 2eq Nem-mld/purified-SH Phosphate buffer 0.1M pH6 | 2eq Nem-mld/purified-SH Phosphate buffer 0.1M pH6 | 2eq Nem-mld/crude-SH Phosphate buffer 0.1M pH6 |
| Nem peptide purification | Kromasil C18 TFA 20%-20 min->40% MeCN | Kromasil C18 TFA 25%-20 min->35% MeCN | Kromasil C18 TFA 24%-20 min->44% MeCN | Kromasil C18 TFA 20%-20 min->40% MeCN | Kromasil C18 TFA 25%-20 min->40% MeCN |
| Nem peptide analytical procedure | Aeris peptide C18 TFA 20%-20 min->40% MeCN | Aeris peptide C18 TFA 25%-20 min->35% MeCN | Aeris peptide C18 TFA 26%-20 min->36% MeCN | Aeris peptide C18 TFA 25%-20 min->35% MeCN | Aeris peptide C18 TFA 24%-20 min->34% MeCN |
| Nem peptide average mass | theor 2848,4156 | theor 5077,1614 | theor 2876,4694 | theor 5105,2152 | theor 2846,4462 |
| Cis/Trans isolated isomers | exp 2848,0354 & 28480269 | exp 5077,0371 & ND | exp 2876,0220 & ND | exp 5104,9678 & ND | exp 2846,4702 & ND |
| Bodipy coupling | 1,1eq Bpy-mld/purified-SH Phosphate buffer 0.1M pH6 | 1,2eq Bpy-mld/purified-SH Phosphate buffer 0.1M pH6 | 2eq Bpy-mld/purified-SH Phosphate buffer 0.1M pH6 | 2eq Bpy-mld/purified-SH Phosphate buffer 0.1M pH6 | 2eq Bpy-mld/purified-SH Phosphate buffer 0.1M pH6 |
| Bodipy peptide purification | Kromasil C18 TFA 25%-20 min->45% MeCN | Kromasil C18 TFA 27%-20 min->37% MeCN | Kromasil C18 TFA 26%-20 min->46% MeCN | Kromasil C18 TFA 25%-20 min->40% MeCN | Kromasil C18 TFA 30%-20 min->40% MeCN |
| Bodipy peptide analytical procedure | Aeris peptide C18 TFA 28%-20 min->38% MeCN | Aeris peptide C18 TFA 27%-20 min->37% MeCN | Aeris peptide C18 TFA 30%-20 min->40% MeCN | Aeris peptide C18 TFA 28%-20 min->38% MeCN | Aeris peptide C18 TFA 27%-20 min->37% MeCN |
| Bodipy peptide average mass | theor 3137,5082 | theor 5366,2540 | theor 3165,5619 | theor 5394,3077 | theor 3135,5387 |
| Cis/Trans isolated isomers | exp 3136,9868 & 3137,0911 | exp 5365,5737 & 5365,7817 | exp 3164,8613 & ND | exp 5393,6948 & ND | exp 3135,2537 & ND |

| R8/S5 oleline incorporation | A303 R₈-A310 S₅ | | I307 R₈-A314 S₅ |
|---|---|---|---|
| Additional modifications | | N-ter Apd sequence | |
| Crude solubility | TFA 0.08% | TFA 0.08% | Formic Acid 10% |
| Free thiol peptide purification procedure | Nucleosil VP C18 TFA 27%-20 min->37% MeCN | MPLC C18 TFA 20%-60 min->60% B | MPLC C18 TFA 20-60->70% B |
| NEM coupling | 4,5eq Nem-mld/purified-SH Phosphate buffer 0.1M pH6 | 3eq Nem-mld/purified-SH Phosphate buffer 0.1M pH6 | 2eq Nem-mld/purified-SH Phosphate buffer 0.1M pH7,2 |
| Nem peptide purification | Kromasil C18 TFA 25%-20 min->35% MeCN (A) 26%-20 min->36% MeCN (B) | Kromasil C18 TFA 25%-20 min->35% MeCN | Kromasil C18 ammonium acetate 50 mM 27%-20 min->37% MeCN |
| Nem peptide analytical procedure | Aeris peptide C18 TFA 25%-20 min->35% MeCN | Aeris peptide C18 TFA 25%-20 min->35% MeCN | Aeris peptide C18 a- TFA 34%-20 min->44% MeCN (-SH) b- ammonium acetate 10 mM 25%-20 min->35% MeCN (-Nem) |
| Nem peptide average mass | theor 29494737 | theor 5178,2232 | theor 3326,9069 |

TABLE II-continued

Purification procedures and mass spectrometry data of all NEMO i,i+7 hydrocarbon-stapled peptides use

| | | | |
|---|---|---|---|
| Cis/Trans isolated isomers | exp 2949,1758 & 2949,8513 | exp ND & 5177,1987 | exp 3326,7917 & 3326,9282 |
| Bodipy coupling | 1,2eq Bpy-mld/purified-SH Phosphate buffer 0.1M pH6 | 1,2eq Bpy-mld/purified-SH Phosphate buffer 0.1M pH6 | Sur -SH (A + B) 1,4eq Phosphate buffer 0.1M pH7,2 |
| Bodipy peptide purification | Kromasil C18 TFA 28%-20 min->38% MeCN (A) & 29%-20 min->39% MeCN (B) | Kromasil C18 TFA 27%-20 min->37% MeCN | Kromasil C18 ammonium acetate 50 mM 30%-20 min->40% MeCN |
| Bodipy peptide analytical procedure | Aeris peptide C18 TFA 28%-20 min->38% MeCN | Aeris peptide C18 TFA 27%-20 min->37% MeCN | Aeris peptide C18 a- TFA 38%-20 min->48% MeCN b- Acetate NH4+ 10 mM 28%-20 min->38% MeCN |
| Bodipy peptide average mass | theor 3238,5700 | theor 5467,3157 | theor 3615,9995 |
| Cis/Trans isolated isomers | exp 3238,3923 & 3238,4163 | exp 5466,7676 & 5466,7246 | exp 3615,9119 & 3615,9663 |

TABLE III

CD data and thermodynamic parameters of UBI-AIB and i + 4 and i + 7 UBI SAHN peptides

PEPTIDES

| | | | Structuration a-helical content at 1° C. | Peptide length aa | Thermal stability (30 µM or 300 µM) ΔCp ≈ 0 | | |
|---|---|---|---|---|---|---|---|
| | | | | | Tm (C°) | ΔH (cal. mol)$^{-1}$ | ΔS (cal. mol$^{-1}$.K$^{-1}$) |
| UBI | UBI | LKAQADIYKARFQAERHAREK (SEQ ID NO: 1) | 42% | 21 | Tm < 0 (-18 ± 0.3) | -5750 | -22 |
| | A-UBI | RQIKIWFQNRRMKWKKLKAQA DIYKARFQAERHAREK (SEQ ID NO: 16) | 46% | 37 | | | |
| AIB | UBI-AIB | LKBQBDIYKBRFQBERHBREK (SEQ ID NO: 17) | 49% | 21 | Tm < 0 (-8 ± 0.3) | -5370 | -20 |
| | A-UBI-AIB | RQIKIWFQNRRMKWKKLKBQB DIYKBRFQBERHBREK (SEQ ID NO: 18) | 43% | 37 | | | |
| Stapled i, i + 4 | UBI-SAHN A310-A314 | LKAQADIYKXRFQXERHAREK (SEQ ID NO: 6) | 65% | 21 | 15 ± 0.3 | -3200 | -11 |
| | A-UBI-SAHN A310-A314 | RQIKIWFQNRRMKWKKLKAQA DIYKXRFQXERHAREK (SEQ ID NO: 7) | 57% | | | | |
| | UBI-SAHN A303-I307 | LKXQADXYKARFQAERHAREK (SEQ ID NO: 4) | 70% | 21 | 19 ± 0.3 | -6900 | -24 |
| | UBI-SAHN D306-A310 | LKAQAXIYKXRFQAERHAREK (SEQ ID NO: 5) | 65% | 21 | 20 ± 0.3 | -5790 | -20 |
| Stapled i, i + 7 | UBI-SAHN D306-Q313 | LKAQAXIYKARFXAERHAREK (SEQ ID NO: 10) | A: 75% - B: 76% | 21 | A ou B: 35 ± 0.3 | A: -4800 - B: -5290 | A: -16 - B: -17 |
| | UBI-SAHN A303-A310 | LKXQADIYKXRFQAERHAREK (SEQ ID NO: 8) | A: 63% - B: 80% | 21 | A: 5 - B: 33 ± 0.3 | A: -5950 - B: -6510 | A: -21 - B: -21 |
| | Co-SAHN I307-A314 | ELAQLQAELDXVQAVVQXDKQ ELRKL (SEQ ID NO: 19) | A: 45% - B: 58% | 26 | A: 21 - B: 32 ± 0.3 | A: -6970 - B: -7200 | A: -24 - B: -24 |

The antennapedia peptide is shown underlined whereas the insertion of hydrocarbon staples and Aib residues are shown by the X and B letters, respectively.

TABLE IV

Binding affinities of UBI-AIB and i + 4 and i + 7 UBI SAHN peptides

PEPTIDES

| | | | Binding affinity (FP) at 10 μM* (μM) | Binding affinity (FP) at 0.1 μM (μM) |
|---|---|---|---|---|
| UBI | UBI | LKAQADIYKARFQAERHAREK (SEQ ID NO: 1) | No complex (>10000) | No complex (>10000) |
| | A-UBI | RQIKIWFQNRRMKWKKLKAQA DIYKARFQAERHAREK (SEQ ID NO: 16) | 22 ± 4 | 4 ± 1 |
| AIB | UBI-AIB | LKBQBDIYKBRFQBERHBREK (SEQ ID NO: 17) | No complex (>10000) | No complex (>10000) |
| | A-UBI-AIB | RQIKIWFQNRRMKWKKLKBQB DIYKBRFQBERHBREK (SEQ ID NO: 18) | 24 ± 3 | 5 ± 2 |
| Stapled i, i + 4 | UBI-SAHN A310-A314 | LKAQADIYKXRFQXERHAREK (SEQ ID NO: 6) | Very weak binding | ≈360 |
| | A-UBI-SAHN A310-A314 | RQIKIWFQNRRMKWKKLKAQA DIYKXRFQXERHAREK (SEQ ID NO: 7) | 21 ± 9 | 0.2 ± 0.05 |
| | UBI-SAHN A303-I307 | LKXQADXYKARFQAERHAREK (SEQ ID NO: 4) | Very weak binding | ≈360 |
| | UBI-SAHN D306-A310 | LKAQAXIYKXRFQAERHAREK (SEQ ID NO: 5) | Not detectable | 85 ± 15 |
| Stapled i, i + 7 | UBI-SAHN D306-Q313 | LKAQAXIYKARFXAERHAREK (SEQ ID NO: 10) | (A) & (B): Very weak binding | (A): 34 ± 6, (B): 71 ± 10 |
| | A-UBI-SAHN D306-Q313 | RQIKIWFQNRRMKWKKLKAQA XIYKARFXAERHAREK (SEQ ID NO: 11) | | (A): 0.06 ± 0.01, (B): 0.05 ± 0.02 |
| | UBI-SAHN A303-A310 | LKXQADIYKXRFQAERHAREK (SEQ ID NO: 8) | (A) & (B): Very weak binding | (A): 76 ± 9, (B): 211 ± 30 |
| | A-UBI-SAHN A303-A310 | RQIKIWFQNRRMKWKKLKXQA DIYKXRFQAERHAREK (SEQ ID NO: 9) | | (A): 0.3 ± 0.1, (B): 0.02 ± 0.01 |
| | Co-UBI-SAHN I307-A314 | ELAQLQAELDXVQAVVQXDKQ ELRKL (SEQ ID NO: 19) | No complex (>10000) | (A) > 1850, (B) > 800 |

TABLE V

NF-κB inhibition of UBI-AIB and i + 4 and i + 7 UBI-SAHN peptides in cell

PEPTIDES

| | | | IC 50 (μM) |
|---|---|---|---|
| UBI | UBI | LKAQADIYKARFQAERHAREK (SEQ ID NO: 1) | N.I* |
| | A-UBI | RQIKIWFQNRRMKWKKLKAQA DIYKARFQAERHAREK (SEQ ID NO: 16) | 4 ± 1 |
| AIB | UBI-AIB | LKBQBDIYKBRFQBERHBREK (SEQ ID NO: 17) | N.I* |
| | A-UBI-AIB | RQIKIWFQNRRMKWKKLKBQB DIYKBRFQBERHBREK (SEQ ID NO: 18) | 1.5 ± 0.5 |
| Stapled i, i + 4 | UBI-SAHN A310-A314 | LKAQADIYKXRFQXERHAREK (SEQ ID NO: 6) | N.I* |
| | A-UBI-SAHN A310-A314 | RQIKIWFQNRRMKWKKLKAQA DIYKXRFQXERHAREK (SEQ ID NO: 7) | 0.43 ± 0.04 |
| | UBI-SAHN A303-I307 | LKXQADXYKARFQAERHAREK (SEQ ID NO: 4) | N.I* |
| | UBI-SAHN D306-A310 | LKAQAXIYKXRFQAERHAREK (SEQ ID NO: 5) | N.I* |

TABLE V-continued

NF-κB inhibition of UBI-AIB and i + 4 and
i + 7 UBI-SAHN peptides in cell

| PEPTIDES | | | IC 50 (μM) |
|---|---|---|---|
| Stapled i, i + 7 | UBI-SAHN D306-Q313 | LKAQAX IYKARFXAERHAREK (SEQ ID NO: 10) | N.I* |
| | A-UBI-SAHN D306-Q313 | RQIKIWFQNRRMKWKKLKAQA XIYKARFXAERHAREK (SEQ ID NO: 11) | (A): 0.6 ± 0.2 |
| | UBI-SAHN A303-A310 | LKXQADIYKXRFQAERHAREK (SEQ ID NO: 8) | N.I* |
| | A-UBI-SAHN A303-A310 | RQIKIWFQNRRMKWKKLKXQA DIYKXRFQAERHAREK (SEQ ID NO: 9) | (B): 0.6 ± 0.1 |
| | Co-SAHN I307-A314 | ELAQLQAELDXVQAVVQXDKQ ELRKL (SEQ ID NO: 19) | N.I* |

*N.I: No inhibition observed

TABLE VI

| SEQ ID NO: | Name | Sequence |
|---|---|---|
| 1 | UBI | LKAQADIYKARFQAERHAREK |
| 2 | General formula | LKX$_1$QAX$_2$X$_3$YK X$_4$RFX$_5$X$_6$X$_7$ RX$_8$ARX$_9$K |
| 3 | Antennapaedia CPP | RQIKIWFQNRRMKWKK |
| 4 | UBI-SAHN A303-I307 | LKX$_1$QADX$_3$YKARFQAERHAREK |
| 5 | UBI-SAHN D306-A310 | LKAQAX$_2$IYKX$_4$RFQAERHAREK |
| 6 | UBI-SAHN A310-A314 | LKAQADIYKX$_4$RFQX$_6$ERHAREK |
| 7 | A-UBI-SAHN A310-A314 | RQIKIWFQNRRMKWKKLKAQAD IYKX$_4$RFQX$_6$ERHAREK |
| 8 | UBI-SAHN A303-A310 | LKX$_1$QADIYKX$_4$RFQAERHAREK |
| 9 | A-UBI-SAHN A303-A310 | RQIKIWFQNRRMKWKKLKX$_1$QA DIYKX$_4$RFQAERHAREK |
| 10 | UBI-SAHN D306-Q313 | LKAQAX$_2$IYKARFX$_5$AERHAREK |
| 11 | A-UBI-SAHN D306-Q313 | RQIKIWFQNRRMKWKKLKAQAX$_2$ IYKARFX$_5$AERHAREK |
| 12 | UBI-SAHN D306-Q313 Q/Q | LKAQAX$_2$IYKARFX$_5$AQRHARQK |
| 13 | A-UBI-SAHN D306-Q313 Q/Q | RQIKIWFQNRRMKWKKLKAQAX$_2$ IYKARFX$_5$AQRHARQK |
| 14 | UBI-SAHN D306-Q313 OMe | LKAQAX$_2$IYKARFX$_5$AX$_7$RHARX$_9$K |
| 15 | A-UBI-SAHN D306-Q313 OMe | RQIKIWFQNRRMKWKKLKAQAX$_2$ IYKARFX$_5$AX$_7$RHARX$_9$K |
| 16 | A-UBI | RQIKIWFQNRRMKWKKLKAQAD IYKARFQAERHAREK |
| 17 | UBI-AIB | LKAibQAibDIYKAibRFQAib ERHAibREK |
| 18 | A-UBI-AIB | RQIKIWFQNRRMKWKKLKAibQ AibDIYKAibRFQAibERHAibREK |
| 19 | Co-UBI-SAHN I307-A314 | ELAQLQAELDXVQAVVQXDKQE LRKL |

REFERENCES

[1] Chiaravalli J, Fontan E, Fsihi H, Coic Y M, Baleux F, Veron M, et al. Direct inhibition of NF-kappaB activation by peptide targeting the NOA ubiquitin binding domain of NEMO. Biochem Pharmacol. 2011; 82:1163-1174.

[2] Altschul S F, Gish W, Miller W, Myers E W, Lipman D J. Basic local alignment search tool. J Mol Biol. 1990; 215:403-410.

[3] Schafmeister C E, Po J, Verdine G L. An all-hydrocarbon cross-linking system for enhancing the helicity and metabolic stability of peptides. J Am Chem Soc. 2000; 122: 5891-5892.

[4] Verdine G L, Hilinski G J. Stapled peptides for intracellular drug targets. Methods Enzymol. 2012; 503:3-33.

[5] Kim Y W, Grossmann T N, Verdine G L. Synthesis of all-hydrocarbon stapled alpha-helical peptides by ring-closing olefin metathesis. Nat protoc. 2011; 6:761-771.

[6] Hilinski G J, Kim Y W, Hong J, Kutchukian P S, Crenshaw C M, Berkovitch S S, et al. Stitched alpha-helical peptides via bis ring-closing metathesis. J Am Chem Soc. 2014; 136:12314-12322.

[7] Agou F, Courtois G, Chiaravalli J, Baleux F, Coic Y M, Traincard F, et al. Inhibition of NF-kappa B activation by peptides targeting NF-kappa B essential modulator (nemo) oligomerization. J Biol Chem. 2004; 279:54248-54257.

[8] Mahalakshmi R, Balaram P. Non-protein amino acids in the design of secondary structure scaffolds. Methods Mol Biol (Clifton, NJ). 2006; 340:71-94.

[9] Yang J T, Wu C S, Martinez H M. Calculation of protein conformation from circular dichroism. Methods Enzymol. 1986; 130:208-269.

[10] Grubisha O, Kaminska M, Duquerroy S, Fontan E, Cordier F, Haouz A, et al. DARPin-assisted crystallography of the CC2-LZ domain of NEMO reveals a coupling between dimerization and ubiquitin binding. J Mol Biol. 2010; 395:89-104.
[11] Greenfield N J. Analysis of circular dichroism data. Methods Enzymol. 2004; 383:282-317.
[12] Chu Q, Moellering R E, Hilinski G J, Kim Y-W, Grossmann T N, Yeh J T H, et al. Towards understanding cell penetration by stapled peptides. Medchemcomm. 2015; 6:111-119.
[13] Young Kim H, Young Yum S, Jang G, Ahn D R. Discovery of a non-cationic cell penetrating peptide derived from membrane-interacting human proteins and its potential as a protein delivery carrier. Sci Rep. 2015; 5:11719.
[14] O'Donnell M A, Hase H, Legarda D, Ting A T. NEMO inhibits programmed necrosis in an NFkappaB-independent manner by restraining RIP1. PloS one. 2012; 7:e41238.
[15] Jackson S S, Oberley C, Hooper C P, Grindle K, Wuerzberger-Davis S, Wolff J, McCool K, Rui L, Miyamoto S. Withaferin A disrupts ubiquitin-based NEMO reorganization induced by canonical NF-κB signaling. Exp Cell Res. 2015; 331(1):58-72.
[16] Fontan L, Yang C, Kabaleeswaran V, Volpon L, Osborne M J, Beltran E, Garcia M, Cerchietti L, Shaknovich R, Yang S N, Fang F, Gascoyne R D, Martinez-Climent J A, Glickman J F, Borden K, Wu H, Melnick A. MALT1 small molecule inhibitors. specifically suppress ABC-DLBCL in vitro and in vivo. Cancer Cell. 2012; 22(6):812-24.
[17] Nagel D, Spranger S, Vincendeau M, Grau M, Raffegerst S, Kloo B, Hlahla D, Neuenschwander M, Peter von Kries J, Hadian K, Dorken B, Lenz P, Lenz G, Schendel D J, Krappmann D. Pharmacologic inhibition of MALT I protease by phenothiazines as a therapeutic approach for the treatment of aggressive ABC-DLBCL. Cancer Cell. 2012; 22(6):825-37.

The invention claimed is:

1. A peptide, comprising an amino sequence (I) which is at least 60% identical to the amino acid sequence SEQ ID NO: 1, and further comprising at least one macrocycle-forming linker connecting a first amino acid to a second amino acid of said sequence (I), wherein the sequence (I) consists of:

LKX$_1$QAX$_2$X$_3$YK X$_4$RFX$_5$X$_6$X$_7$R X$_8$ARX$_9$K,  (SEQ ID NO: 2)

in which:
- X$_1$ is A;
- X$_2$ is a cross-linked amino acid;
- X$_3$ is I;
- X$_4$ is A;
- X$_5$ is a cross-linked amino acid;
- X$_6$ is A;
- X$_7$ is E;
- X$_8$ is H or Q; and
- X$_9$ is E;

providing that X$_2$ and X$_5$ are cross-linked by the macrocycle-forming linker.

2. The peptide according to claim 1, which further comprises a cell-penetrating peptide sequence fused to the N-terminus of the sequence (I).

3. The peptide according to claim 2, wherein said cell-penetrating peptide sequence is SEQ ID NO: 3.

4. The peptide according to claim 1, wherein each amino acid connected by the macrocycle-forming linker is a α,α-disubstituted amino acid.

5. The peptide according to claim 1, wherein the macrocycle forming linker is a C$_4$ to C$_{18}$ alkenylene.

6. The peptide according to claim 1, which is selected from the group consisting of:

LKAQAX$_2$IYKARFX$_5$AERHAREK  (SEQ ID NO: 10)
and
RQIKIWFQNRRMKWKKLKAQAX$_2$IYKARFX$_5$AERHAREK,  (SEQ ID NO: 11)

wherein the residues X$_2$, and X$_5$ are α,α-disubstituted amino acids comprising an α-methyl, and wherein the pair of residues X$_2$ and X$_5$ of the sequences SEQ ID NO: 10 to 11 are connected by a C$_{11}$ alkenylene macrocycle forming linker.

7. A method of preparing the peptide according to claim 1, comprising the steps of:
- a) synthesizing the amino acid sequence of the peptide according to claim 1, and
- b) connecting two amino acids of the sequence obtained in a) through a macrocycle containing linker.

8. The method according to claim 7, wherein step a) comprises incorporating two α,α-disubstituted in the amino acid sequence of the peptide, wherein said amino acids are substituted with a methyl and a C$_3$ to C$_{10}$ alkenyl and separated by an intervening sequence of 3 or 6 amino acids.

9. The method according to claim 8, wherein each α,α-disubstituted amino acid comprises a 4'-pentenyl in S configuration, and said α,α-disubstituted amino acids are separated by an intervening sequence of 3 amino acids.

10. The method according to claim 8, wherein a first α,α-disubstituted amino acid comprises a 7'-octenyl in R configuration and a second α,α-disubstituted α-amino acid comprises a 4'-pentenyl in S configuration, and said α,α-disubstituted amino acids are separated by an intervening sequence of 6 amino acids.

11. The method according to claim 8, wherein step b) comprises, connecting the alkenyl side-chains of the α,α-disubstituted amino acids by olefin methatesis so as to form a C$_4$ to C$_{18}$ alkenylene macrocycle linker.

12. A pharmaceutical composition comprising at least a peptide according to claim 1 and a pharmaceutically acceptable vehicle.

13. The pharmaceutical composition according to claim 12, for use as anti-inflammatory or anticancer medicament.

14. The peptide according to claim 1, wherein the peptide has the sequence SEQ ID NO: 10 and wherein X$_2$ and X$_5$ are cross-linked by the macrocycle-forming linker.

15. The peptide according to claim 1, wherein the peptide has the sequence SEQ ID NO: 11 and wherein X$_2$ and X$_5$ are cross-linked by the macrocycle-forming linker.

* * * * *

SEQUENCE LISTING

```
<160> NUMBER OF SEQ ID NOS: 19

<210> SEQ ID NO 1
<211> LENGTH: 21
<212> TYPE: PRT
<213> ORGANISM: artificial sequence
<220> FEATURE:
<223> OTHER INFORMATION: synthetic peptide

<400> SEQUENCE: 1

Leu Lys Ala Gln Ala Asp Ile Tyr Lys Ala Arg Phe Gln Ala Glu Arg
1               5                   10                  15

His Ala Arg Glu Lys
            20

<210> SEQ ID NO 2
<211> LENGTH: 21
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (3)..(3)
<223> OTHER INFORMATION: Xaa is Alanine or a cross-linked amino acid
<220> FEATURE:
<221> NAME/KEY: misc_feature
<222> LOCATION: (6)..(7)
<223> OTHER INFORMATION: Xaa (6) is Aspartic acid, a cross-linked or
      neutral amino acid Xaa (7) is Isoleucine or a cross-linked amino
      acid
<220> FEATURE:
<221> NAME/KEY: misc_feature
<222> LOCATION: (10)..(10)
<223> OTHER INFORMATION: Xaa is Alanine or a cross-linked amino acid
<220> FEATURE:
<221> NAME/KEY: misc_feature
<222> LOCATION: (13)..(15)
<223> OTHER INFORMATION: Xaa (13) is Glutamine  or a cross-linked amino
      acid Xaa (14) is Alanine or a cross-linked amino acid
      Xaa (15) is Glutamic acid, a neutral amino acid or a basic amino
      acid
<220> FEATURE:
<221> NAME/KEY: misc_feature
<222> LOCATION: (17)..(17)
<223> OTHER INFORMATION: Xaa is Histidine or Glutamine
<220> FEATURE:
<221> NAME/KEY: misc_feature
<222> LOCATION: (20)..(20)
```

<223> OTHER INFORMATION: Xaa is Glutamic acid, a neutral amino acid or a
      basic amino acid

<400> SEQUENCE: 2

Leu Lys Xaa Gln Ala Xaa Xaa Tyr Lys Xaa Arg Phe Xaa Xaa Xaa Arg
1               5                   10                  15

Xaa Ala Arg Xaa Lys
            20

<210> SEQ ID NO 3
<211> LENGTH: 16
<212> TYPE: PRT
<213> ORGANISM: artificial sequence
<220> FEATURE:
<223> OTHER INFORMATION: synthetic peptide

<400> SEQUENCE: 3

Arg Gln Ile Lys Ile Trp Phe Gln Asn Arg Arg Met Lys Trp Lys Lys
1               5                   10                  15

<210> SEQ ID NO 4
<211> LENGTH: 21
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (3)..(3)
<223> OTHER INFORMATION: Xaa a cross-linked amino acid
<220> FEATURE:
<221> NAME/KEY: misc_feature
<222> LOCATION: (7)..(7)
<223> OTHER INFORMATION: Xaa is a cross-linked amino acid

<400> SEQUENCE: 4

Leu Lys Xaa Gln Ala Asp Xaa Tyr Lys Ala Arg Phe Gln Ala Glu Arg
1               5                   10                  15

His Ala Arg Glu Lys
            20

<210> SEQ ID NO 5
<211> LENGTH: 21
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (6)..(6)
<223> OTHER INFORMATION: Xaa is a cross-linked amino acid
<220> FEATURE:
<221> NAME/KEY: misc_feature
<222> LOCATION: (10)..(10)
<223> OTHER INFORMATION: Xaa is a cross-linked amino acid

<400> SEQUENCE: 5

Leu Lys Ala Gln Ala Xaa Ile Tyr Lys Xaa Arg Phe Gln Ala Glu Arg
1               5                   10                  15

His Ala Arg Glu Lys
            20

<210> SEQ ID NO 6
<211> LENGTH: 21
<212> TYPE: PRT
<213> ORGANISM: artificial sequence
<220> FEATURE:
<223> OTHER INFORMATION: synthetic peptide

```
<220> FEATURE:
<221> NAME/KEY: misc_feature
<222> LOCATION: (10)..(10)
<223> OTHER INFORMATION: Xaa is a cross-linked amino acid
<220> FEATURE:
<221> NAME/KEY: misc_feature
<222> LOCATION: (14)..(14)
<223> OTHER INFORMATION: Xaa is a cross-linked amino acid

<400> SEQUENCE: 6

Leu Lys Ala Gln Ala Asp Ile Tyr Lys Xaa Arg Phe Gln Xaa Glu Arg
1               5                   10                  15

His Ala Arg Glu Lys
            20

<210> SEQ ID NO 7
<211> LENGTH: 37
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (26)..(26)
<223> OTHER INFORMATION: Xaa is a cross-linked amino acid
<220> FEATURE:
<221> NAME/KEY: misc_feature
<222> LOCATION: (30)..(30)
<223> OTHER INFORMATION: Xaa is a cross-linked amino acid

<400> SEQUENCE: 7

Arg Gln Ile Lys Ile Trp Phe Gln Asn Arg Arg Met Lys Trp Lys Lys
1               5                   10                  15

Leu Lys Ala Gln Ala Asp Ile Tyr Lys Xaa Arg Phe Gln Xaa Glu Arg
            20                  25                  30

His Ala Arg Glu Lys
            35

<210> SEQ ID NO 8
<211> LENGTH: 21
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (3)..(3)
<223> OTHER INFORMATION: Xaa is a cross-linked amino acid
<220> FEATURE:
<221> NAME/KEY: misc_feature
<222> LOCATION: (10)..(10)
<223> OTHER INFORMATION: Xaa is a cross-linked amino acid

<400> SEQUENCE: 8

Leu Lys Xaa Gln Ala Asp Ile Tyr Lys Xaa Arg Phe Gln Ala Glu Arg
1               5                   10                  15

His Ala Arg Glu Lys
            20

<210> SEQ ID NO 9
<211> LENGTH: 37
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (19)..(19)
<223> OTHER INFORMATION: Xaa is a cross-linked amino acid
```

```
<220> FEATURE:
<221> NAME/KEY: misc_feature
<222> LOCATION: (26)..(26)
<223> OTHER INFORMATION: Xaa is a cross-linked amino acid

<400> SEQUENCE: 9

Arg Gln Ile Lys Ile Trp Phe Gln Asn Arg Arg Met Lys Trp Lys Lys
1               5                   10                  15

Leu Lys Xaa Gln Ala Asp Ile Tyr Lys Xaa Arg Phe Gln Ala Glu Arg
            20                  25                  30

His Ala Arg Glu Lys
        35

<210> SEQ ID NO 10
<211> LENGTH: 21
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (6)..(6)
<223> OTHER INFORMATION: Xaa is a cross-linked amino acid
<220> FEATURE:
<221> NAME/KEY: misc_feature
<222> LOCATION: (13)..(13)
<223> OTHER INFORMATION: Xaa is a cross-linked amino acid

<400> SEQUENCE: 10

Leu Lys Ala Gln Ala Xaa Ile Tyr Lys Ala Arg Phe Xaa Ala Glu Arg
1               5                   10                  15

His Ala Arg Glu Lys
            20

<210> SEQ ID NO 11
<211> LENGTH: 37
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (22)..(22)
<223> OTHER INFORMATION: Xaa is a cross-linked amino acid
<220> FEATURE:
<221> NAME/KEY: misc_feature
<222> LOCATION: (29)..(29)
<223> OTHER INFORMATION: Xaa is a cross-linked amino acid

<400> SEQUENCE: 11

Arg Gln Ile Lys Ile Trp Phe Gln Asn Arg Arg Met Lys Trp Lys Lys
1               5                   10                  15

Leu Lys Ala Gln Ala Xaa Ile Tyr Lys Ala Arg Phe Xaa Ala Glu Arg
            20                  25                  30

His Ala Arg Glu Lys
        35

<210> SEQ ID NO 12
<211> LENGTH: 21
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (6)..(6)
<223> OTHER INFORMATION: Xaa is a cross-linked amino acid
<220> FEATURE:
```

```
<221> NAME/KEY: misc_feature
<222> LOCATION: (13)..(13)
<223> OTHER INFORMATION: Xaa is a cross-linked amino acid

<400> SEQUENCE: 12

Leu Lys Ala Gln Ala Xaa Ile Tyr Lys Ala Arg Phe Xaa Ala Gln Arg
1               5                   10                  15

His Ala Arg Gln Lys
            20

<210> SEQ ID NO 13
<211> LENGTH: 37
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (22)..(22)
<223> OTHER INFORMATION: Xaa is a cross-linked amino acid
<220> FEATURE:
<221> NAME/KEY: misc_feature
<222> LOCATION: (29)..(29)
<223> OTHER INFORMATION: Xaa is a cross-linked amino acid

<400> SEQUENCE: 13

Arg Gln Ile Lys Ile Trp Phe Gln Asn Arg Arg Met Lys Trp Lys Lys
1               5                   10                  15

Leu Lys Ala Gln Ala Xaa Ile Tyr Lys Ala Arg Phe Xaa Ala Gln Arg
            20                  25                  30

His Ala Arg Gln Lys
        35

<210> SEQ ID NO 14
<211> LENGTH: 21
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (6)..(6)
<223> OTHER INFORMATION: Xaa is a cross-linked amino acid
<220> FEATURE:
<221> NAME/KEY: misc_feature
<222> LOCATION: (13)..(13)
<223> OTHER INFORMATION: Xaa is a cross-linked amino acid
<220> FEATURE:
<221> NAME/KEY: misc_feature
<222> LOCATION: (15)..(15)
<223> OTHER INFORMATION: Xaa is Glutamic acid methyl ester
<220> FEATURE:
<221> NAME/KEY: misc_feature
<222> LOCATION: (20)..(20)
<223> OTHER INFORMATION: Xaa is Glutamic acid methyl ester

<400> SEQUENCE: 14

Leu Lys Ala Gln Ala Xaa Ile Tyr Lys Ala Arg Phe Xaa Ala Xaa Arg
1               5                   10                  15

His Ala Arg Xaa Lys
            20

<210> SEQ ID NO 15
<211> LENGTH: 37
<212> TYPE: PRT
<213> ORGANISM: artificial sequence
<220> FEATURE:
<223> OTHER INFORMATION: synthetic peptide
<220> FEATURE:
```

```
<221> NAME/KEY: misc_feature
<222> LOCATION: (22)..(22)
<223> OTHER INFORMATION: Xaa is is a cross-linked amino acid
<220> FEATURE:
<221> NAME/KEY: misc_feature
<222> LOCATION: (29)..(29)
<223> OTHER INFORMATION: Xaa is is a cross-linked amino acidr
<220> FEATURE:
<221> NAME/KEY: misc_feature
<222> LOCATION: (31)..(31)
<223> OTHER INFORMATION: Xaa is Glutamic acid methyl ester
<220> FEATURE:
<221> NAME/KEY: misc_feature
<222> LOCATION: (36)..(36)
<223> OTHER INFORMATION: Xaa is Glutamic acid methyl ester

<400> SEQUENCE: 15

Arg Gln Ile Lys Ile Trp Phe Gln Asn Arg Arg Met Lys Trp Lys Lys
1               5                   10                  15

Leu Lys Ala Gln Ala Xaa Ile Tyr Lys Ala Arg Phe Xaa Ala Xaa Arg
            20                  25                  30

His Ala Arg Xaa Lys
        35

<210> SEQ ID NO 16
<211> LENGTH: 37
<212> TYPE: PRT
<213> ORGANISM: artificial sequence
<220> FEATURE:
<223> OTHER INFORMATION: synthetic peptide

<400> SEQUENCE: 16

Arg Gln Ile Lys Ile Trp Phe Gln Asn Arg Arg Met Lys Trp Lys Lys
1               5                   10                  15

Leu Lys Ala Gln Ala Asp Ile Tyr Lys Ala Arg Phe Gln Ala Glu Arg
            20                  25                  30

His Ala Arg Glu Lys
        35

<210> SEQ ID NO 17
<211> LENGTH: 21
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (3)..(3)
<223> OTHER INFORMATION: Xaa is 2-Aminoisobutyric acid (Aib)
<220> FEATURE:
<221> NAME/KEY: misc_feature
<222> LOCATION: (5)..(5)
<223> OTHER INFORMATION: Xaa is 2-Aminoisobutyric acid (Aib)
<220> FEATURE:
<221> NAME/KEY: misc_feature
<222> LOCATION: (10)..(10)
<223> OTHER INFORMATION: Xaa is 2-Aminoisobutyric acid (Aib)
<220> FEATURE:
<221> NAME/KEY: misc_feature
<222> LOCATION: (14)..(14)
<223> OTHER INFORMATION: Xaa is 2-Aminoisobutyric acid (Aib)
<220> FEATURE:
<221> NAME/KEY: misc_feature
<222> LOCATION: (18)..(18)
<223> OTHER INFORMATION: Xaa is 2-Aminoisobutyric acid (Aib)

<400> SEQUENCE: 17

Leu Lys Xaa Gln Xaa Asp Ile Tyr Lys Xaa Arg Phe Gln Xaa Glu Arg
1               5                   10                  15
```

His Xaa Arg Glu Lys
        20

<210> SEQ ID NO 18
<211> LENGTH: 37
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (19)..(19)
<223> OTHER INFORMATION: Xaa is 2-Aminoisobutyric acid (Aib)
<220> FEATURE:
<221> NAME/KEY: misc_feature
<222> LOCATION: (21)..(21)
<223> OTHER INFORMATION: Xaa is 2-Aminoisobutyric acid (Aib)
<220> FEATURE:
<221> NAME/KEY: misc_feature
<222> LOCATION: (26)..(26)
<223> OTHER INFORMATION: Xaa is 2-Aminoisobutyric acid (Aib)
<220> FEATURE:
<221> NAME/KEY: misc_feature
<222> LOCATION: (30)..(30)
<223> OTHER INFORMATION: Xaa is 2-Aminoisobutyric acid (Aib)
<220> FEATURE:
<221> NAME/KEY: misc_feature
<222> LOCATION: (34)..(34)
<223> OTHER INFORMATION: Xaa is 2-Aminoisobutyric acid (Aib)

<400> SEQUENCE: 18

Arg Gln Ile Lys Ile Trp Phe Gln Asn Arg Arg Met Lys Trp Lys Lys
1               5                   10                  15

Leu Lys Xaa Gln Xaa Asp Ile Tyr Lys Xaa Arg Phe Gln Xaa Glu Arg
            20                  25                  30

His Xaa Arg Glu Lys
        35

<210> SEQ ID NO 19
<211> LENGTH: 26
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (11)..(11)
<223> OTHER INFORMATION: Xaa is is a cross-linked amino acid
<220> FEATURE:
<221> NAME/KEY: misc_feature
<222> LOCATION: (18)..(18)
<223> OTHER INFORMATION: Xaa is is a cross-linked amino acid

<400> SEQUENCE: 19

Glu Leu Ala Gln Leu Gln Ala Glu Leu Asp Xaa Val Gln Ala Val Val
1               5                   10                  15

Gln Xaa Asp Lys Gln Glu Leu Arg Lys Leu
            20                  25